(12) United States Patent
Adriany et al.

(10) Patent No.: US 10,267,515 B2
(45) Date of Patent: Apr. 23, 2019

(54) FRACTAL FLUID PASSAGES APPARATUS

(71) Applicant: Additive Rocket Corporation, Oceanside, CA (US)

(72) Inventors: Kyle Adriany, San Diego, CA (US); Elyce Bayat, Pleasanton, CA (US); Nicholas Garrett, Victorville, CA (US); Ryan Pedersen, Walnut, CA (US); Reiley Weekes, San Diego, CA (US); Anthony Tran, Monterey Park, CA (US)

(73) Assignee: Additive Rocket Corporation, Oceanside, CA (US)

( * ) Notice: Subject to any disclaimer, the term of this patent is extended or adjusted under 35 U.S.C. 154(b) by 0 days.

(21) Appl. No.: 15/699,851

(22) Filed: Sep. 8, 2017

(65) Prior Publication Data

US 2018/0087701 A1 Mar. 29, 2018

Related U.S. Application Data

(60) Provisional application No. 62/385,122, filed on Sep. 8, 2016.

(51) Int. Cl.
*F23D 14/22* (2006.01)
*B29C 45/27* (2006.01)
(Continued)

(52) U.S. Cl.
CPC .......... *F23D 14/22* (2013.01); *B01J 19/2485* (2013.01); *B29C 45/2725* (2013.01);
(Continued)

(58) Field of Classification Search
CPC ......... F16L 41/02; F16L 41/03; F16L 41/023; Y10T 137/85938; B01J 2219/247;
(Continued)

(56) References Cited

U.S. PATENT DOCUMENTS 3,381,336 A * 5/1968 Wells ...................... B29C 47/30
118/410
3,561,053 A * 2/1971 Pearson .................. B29C 47/26
425/192 R (Continued)

OTHER PUBLICATIONS

International Search Report for PCT/US17/050790, 2 pages, dated Nov. 12, 2017.
(Continued)

*Primary Examiner* — Atif H Chaudry
(74) *Attorney, Agent, or Firm* — K&L Gates LLP; Jordan A. Kwan

(57) ABSTRACT

Aspects of the present disclosure include branching fluid passages in an apparatus that reduce turbulent flow and generate evenly distributed fluid pressure as the fluids branch off into the different passages. In some embodiments, the branching passages may be subdivided into two sets: the branching passages for the liquid fuel and the branching passages for the liquid oxidizer. In some embodiments, the two sets of passages are carefully designed in an elegant yet extremely intricate manner that is optimized for proper fluid flow and maximal burn efficiency. The ends of all of the passages meet at the injector interface, which dispense the liquids into the combustion chamber for ignition. Generally, these designs are achieved through additive manufacturing, and would be extremely difficult, if not impossible, to be manufactured using traditional techniques.

20 Claims, 28 Drawing Sheets

(51) Int. Cl.
  *F02M 61/16* (2006.01)
  *G01N 30/60* (2006.01)
  *F16L 41/02* (2006.01)
  *B01J 19/24* (2006.01)
  *F23R 3/28* (2006.01)
  *F02M 35/10* (2006.01)
  *B33Y 80/00* (2015.01)
  *F16L 41/03* (2006.01)
  *F02M 61/18* (2006.01)

(52) U.S. Cl.
  CPC ....... *B33Y 80/00* (2014.12); *F02M 35/10347* (2013.01); *F02M 61/16* (2013.01); *F02M 61/1806* (2013.01); *F16L 41/02* (2013.01); *F16L 41/023* (2013.01); *F16L 41/03* (2013.01); *F23R 3/28* (2013.01); *G01N 30/6017* (2013.01); *B01J 2219/247* (2013.01); *B01L 2300/0864* (2013.01); *B01L 2300/0874* (2013.01); *Y10T 137/85938* (2015.04)

(58) Field of Classification Search
  CPC ......... B01J 19/2485; F23R 3/28; F23D 14/22; G01N 30/6017; B33Y 80/00; B01L 2300/0864; B01L 2300/0874; F02M 35/10347; B29C 45/2725
  See application file for complete search history.

(56) References Cited

U.S. PATENT DOCUMENTS

| | | | |
|---|---|---|---|
| 4,917,146 A * | 4/1990 | Sundheimer | F22B 37/228 137/561 A |
| 2004/0213084 A1 | 10/2004 | Kearney et al. | |
| 2009/0162731 A1 | 6/2009 | Gaudillat | |
| 2009/0274549 A1 | 11/2009 | Mitchell et al. | |
| 2012/0074051 A1* | 3/2012 | Gebauer | G01N 30/6017 210/198.2 |

OTHER PUBLICATIONS

Written Opinion of the International Searching Authority for PCT/US17/050790, 5 pages, dated Nov. 12, 2017.

* cited by examiner

FRACTAL FLUID PASSAGES APPARATUS

CROSS REFERENCE TO RELATED APPLICATION

This application claims the benefit of U.S. Provisional Application 62/385,122, filed Sep. 8, 2016, and titled "FRACTAL FLUID PASSAGES APPARATUS," the disclosure of which is hereby incorporated herein in its entirety and for all purposes.

TECHNICAL FIELD

The subject matter disclosed herein generally relates to structures for injecting, distributing, and/or mixing. More specifically, the present disclosures relate to fractal fluid passages in apparatuses with various industrial applicability.

BACKGROUND

Conventionally, channels for allowing the flow of fluid are manufactured using subtractive manufacturing methods, meaning that larger pieces of material are used which are whittled down and bored through until a desired structure is created. These designs are therefore limited by the manufacturing methods employed. In addition, structures with fluid passages are conventionally built with multiple pieces, needing to be welded and fastened together. For ease of manufacturing and replicability, these fluid passages designs therefore exhibit numerous failure points or other high stress areas. In addition, due to utilizing more reliable subtractive manufacturing methods, optimal geometries for providing minimally turbulent and evenly distributed fluid passages are not used. It is desirable therefore to develop new ways of generating apparatuses having fluid passages and their various components.

BRIEF SUMMARY

Aspects of the present disclosure are presented for apparatuses with optimized fluid passages for ensuring proper mass flows that may be created using additive manufacturing techniques.

In some embodiments, an apparatus is presented including: a plurality of fractal fluid passages comprising: an inlet; a first fractal fluid branching passage and a second fractal fluid branching passage, the first and second fractal fluid branching passages coupled to the inlet with continuously smooth curvature to the inlet such that fluid flowing from the inlet is configured to flow into both the first and second fractal fluid branching passages with minimal change in pressure drop; a third fractal fluid branching passage and a fourth fractal fluid branching passage, the third and fourth fractal fluid branching passages coupled to the first fractal fluid branching passage with continuously smooth curvature to the first fractal fluid branching passage such that the fluid flowing from the first fractal fluid branching passage is configured to flow into both the third and fourth fractal fluid branching passages with minimal change in pressure drop; and a fifth fractal fluid branching passage and a sixth fractal fluid branching passage, the fifth and sixth fractal fluid branching passages coupled to the second fractal fluid branching passage with continuously smooth curvature to the second fractal fluid branching passage such that the fluid flowing from the second fractal fluid branching passage is configured to flow into both the fifth and sixth fractal fluid branching passages with minimal change in pressure drop; wherein the plurality of fractal fluid passages are additively manufactured.

In some embodiments, the apparatus further includes: a first orifice leading out an end of the third fractal fluid branching passage; a second orifice leading out an end of the fourth fractal fluid branching passage; a third orifice leading out an end of the fifth fractal fluid branching passage; and a fourth orifice leading out an end of the sixth fractal fluid branching passage; wherein each of the first, second, third, and fourth orifices are configured to allow the fluid to exit the plurality of fractal fluid passages at a substantially uniform mass flow.

In some embodiments of the apparatus, the third fractal fluid branching passage is angled differently than the fifth fractal fluid branching passage such that the fluid exiting from the first orifice is ejected at a different angle than the fluid exiting from the third orifice.

In some embodiments of the apparatus: the inlet comprises an inlet cross-sectional area; the first fractal fluid branching passage comprises a first cross-sectional area; the second fractal fluid branching passage comprises a second cross-sectional area; the third fractal fluid branching passage comprises a third cross-sectional area; the fourth fractal fluid branching passage comprises a fourth cross-sectional area; the fifth fractal fluid branching passage comprises a fifth cross-sectional area; the sixth fractal fluid branching passage comprises a sixth cross-sectional area; the sum of the first cross-sectional area and the second cross-sectional area equals the inlet cross-sectional area; and the sum of the third cross-sectional area, the fourth cross-sectional area, the fifth cross-sectional area and the sixth cross-sectional area equals the inlet cross-sectional area.

In some embodiments of the apparatus, the fluid flows through each of the inlet, the first fractal fluid branching passage, the second fractal fluid branching passage, the third fractal fluid branching passage, the fourth fractal fluid branching passage, the fifth fractal fluid branching passage, and the sixth fractal fluid branching passage at a uniform velocity.

In some embodiments of the apparatus, the fluid flows through each of the inlet, the first fractal fluid branching passage, the second fractal fluid branching passage, the third fractal fluid branching passage, the fourth fractal fluid branching passage, the fifth fractal fluid branching passage, and the sixth fractal fluid branching passage at a uniform pressure.

In some embodiments, the apparatus further includes: a first orifice leading out an end of the third fractal fluid branching passage; a second orifice leading out an end of the fourth fractal fluid branching passage; a third orifice leading out an end of the fifth fractal fluid branching passage; a fourth orifice leading out an end of the sixth fractal fluid branching passage; wherein: the first orifice is configured to allow the fluid to exit the plurality of fractal fluid passages at a first predetermined mass flow; the second orifice is configured to allow the fluid to exit the plurality of fractal fluid passages at a second predetermined mass flow; the third orifice is configured to allow the fluid to exit the plurality of fractal fluid passages at a third predetermined mass flow; and the fourth orifice is configured to allow the fluid to exit the plurality of fractal fluid passages at a fourth predetermined mass flow.

In some embodiments of the apparatus, each of the first, second, third, and fourth orifices are configured to allow the fluid to exit the plurality of fractal fluid passages at a uniform velocity.

In some embodiments of the apparatus, the first fractal fluid branching passage, the second fractal fluid branching passage, the third fractal fluid branching passage, the fourth fractal fluid branching passage, the fifth fractal fluid branching passage, and the sixth fractal fluid branching passage are asymmetrically shaped from one another.

In some embodiments of the apparatus, the plurality of fractal fluid passages is a first plurality of fractal fluid passages, and the fluid is a first fluid, wherein the apparatus further comprises a second plurality of fractal fluid passages configured to allow a second fluid different from the first fluid to flow through the second plurality of fractal fluid passages simultaneously with the flow of the first fluid through the first plurality of fractal fluid passages.

In some embodiments the apparatus, further includes an injector interface partially enclosing a chamber and comprising the first, second, third, and fourth orifices such that the first fluid exits the first plurality of fractal fluid passages through the injector interface and into the chamber via the first, second, third, and fourth orifices.

In some embodiments of the apparatus, the second plurality of fractal fluid passages comprises a second plurality of orifices, and the injector interface further comprises the second plurality of orifices such that the second fluid exits the second plurality of fractal fluid passages through the injector interface and into the chamber via the second plurality of orifices.

In some embodiments of the apparatus, the second fluid exits the injector interface via at least a portion of the second plurality of orifices at a different angle than the first fluid exiting the injector interface.

In some embodiments of the apparatus, at least a portion of the second fluid exits the injector interface at an angle toward the first orifice of the first plurality of fractal fluid passages such that at least said portion of the second fluid collides with the first fluid exiting the first orifice through the injector interface.

In some embodiments the apparatus further includes a plurality of regenerative cooling channels, and wherein the second plurality of fractal fluid passages is coupled to the plurality of regenerative cooling channels such that the second fluid is configured to flow through the plurality of regenerative cooling channels and into the second plurality of fractal fluid passages.

In some embodiments of the apparatus: a first fractal fluid passage of the second plurality of fractal fluid passages includes a first portion of the passage configured to cause fluid to flow in a direction the same as a first direction of the first plurality of fractal fluid passages; and said first fractal fluid passage of the second plurality of fractal fluid passages further includes a second portion of the passage configured to cause fluid to flow in a direction opposite as the first direction of the first plurality of fractal fluid passages.

In some embodiments, the apparatus, further includes a fluid diverter comprising an annulus with progressively decreasing cross-sectional area.

In some embodiments of the apparatus, the plurality of fractal fluid passages further comprises a seventh fractal fluid branching passage and an eighth fractal fluid branching passage, wherein: the seventh fractal fluid branching passage is coupled to the first fractal fluid branching passage with continuously smooth curvature to the first fractal fluid branching passage such that the fluid flowing from the first fractal fluid branching passage is configured to flow into the third, fourth, and seventh fractal fluid branching passages with minimal change in pressure drop; and the eighth fractal fluid branching passage is coupled to the second fractal fluid branching passage with continuously smooth curvature to the second fractal fluid branching passage such that the fluid flowing from the second fractal fluid branching passage is configured to flow into the fifth, and sixth and eighth fractal fluid branching passages with minimal change in pressure drop.

In some embodiments another apparatus is presented that includes: a plurality of fractal fluid passages including: an inlet; a fluid diverter coupled to the inlet and comprising an annulus with progressively decreasing cross-sectional area; a first fractal fluid branching passage coupled to the fluid diverter; a second fractal fluid branching passage coupled to the fluid diverter and having an equal cross-sectional area to the first fractal fluid branching passage; a third fractal fluid branching passage and a fourth fractal fluid branching passage, the third and fourth fractal fluid branching passages coupled to the first fractal fluid branching passage with continuously smooth curvature to the first fractal fluid branching passage such that the fluid flowing from the first fractal fluid branching passage is configured to flow into both the third and fourth fractal fluid branching passages with minimal change in pressure drop; and a fifth fractal fluid branching passage and a sixth fractal fluid branching passage, the fifth and sixth fractal fluid branching passages coupled to the second fractal fluid branching passage with continuously smooth curvature to the second fractal fluid branching passage such that the fluid flowing from the second fractal fluid branching passage is configured to flow into both the fifth and sixth fractal fluid branching passages with minimal change in pressure drop.

In some embodiments of the apparatus, fluid is configured to flow from the inlet and into the fluid diverter, then into the first fractal fluid branching passage, and then into the second fractal fluid branching passage; and wherein the fluid flows into the first and second fractal fluid branching passages with uniform pressure simultaneously.

BRIEF DESCRIPTION OF THE DRAWINGS

Some embodiments are illustrated by way of example and not limitation in the figures of the accompanying drawings.

DETAILED DESCRIPTION

Figure 1:
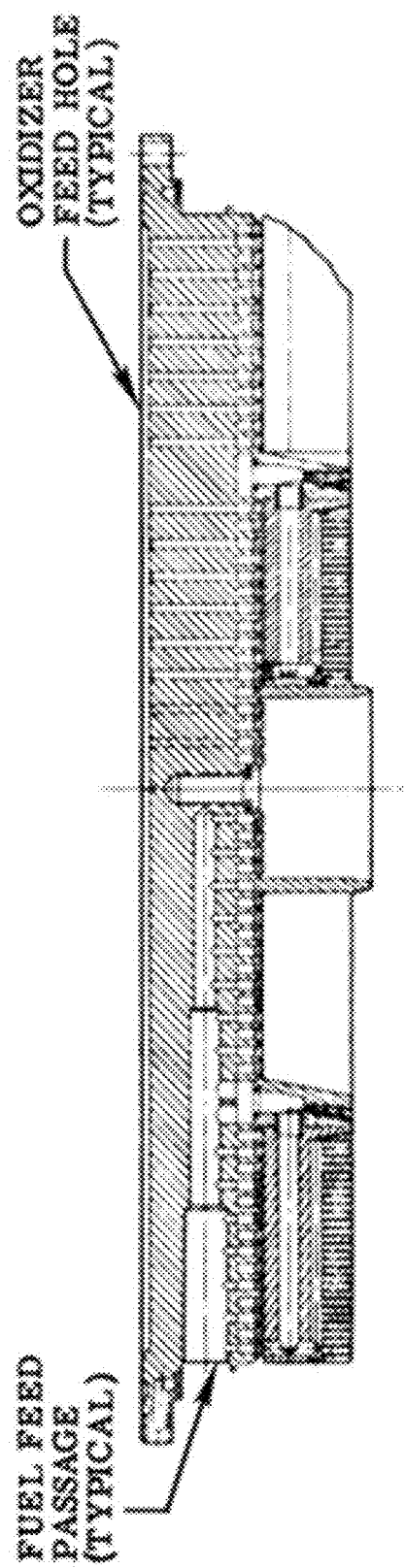
FIG. 1 shows an illustration of an example of a typical injector plate collection chamber and orifice.

Building fluid passages in an apparatus tends to rely on traditional, subtractive, manufacturing methods for their production. As a result, their designs reflect the limitations of the manufacturing methods employed. The passages, for example, built in engines or other large machines are typically created in more than one piece, and are welded or fastened together, using o-rings or other gaskets to seal high pressure regions. These designs exhibit numerous failure points. The designs for fluid passages can be improved to reduce stress points and create more even flow throughout.

Producing an apparatus possessing one or more series of fluid passages through additive manufacturing (AM) offers a multitude of previously unseen improvements. The ability to print a these passages in a single piece using AM techniques increases durability and usability while reducing weight. The speed at which additive manufacturing methods are able to produce components outpaces even the most agile traditional manufacturing operation, as well. The ability to produce novel geometries, which were not previously achievable using traditional manufacturing, has opened the door to countless performance improvements.

The additive manufacturing approach enables the production of even the most complex geometries. This allows designers to create optimized structures without the burden of designing for traditional manufacturing techniques.

Aspects of the present disclosure are presented for apparatuses with optimized fluid passages for ensuring proper mass flows that may be created using additive manufacturing techniques. The apparatus may be placed in various industrial contexts, such as in engine design, chemical distributors, and mixers involving one or more fluids. The apparatus may be generated as a single piece, having no joints, fasteners, or any other areas that could present a risk for damage. The designs are described may also reduce the weight, due to eliminating the need for fasteners and other extraneous hardware. In general, the weight of the apparatus may be optimized to also preclude the inclusion of extraneous material around needed structures. Also, the apparatus may be designed to be highly energy efficient, with optimal flows for fuel and other fluid with minimal head loss while maintaining higher pressures.

In some embodiments, the fluid passages that feed into an injector, including the liquid fuel passages and the liquid oxidizer passages, are arranged in a branching fashion, not unlike the shapes of tree roots or branching blood vessels. Generally, the fluid passages are designed with smooth, continuous curvature, compared to conventional methods that introduce sharp, perpendicular channels, so as to reduce turbulent flow of the fluid while changing directions. Methods used to develop the fluid passages may have been constrained to develop passages that reduce turbulence and create evenly distributed fluid pressure through each of the passages.

In some embodiments, an injector interface that sometimes defines the end of the fluid passages may include an intermingling of liquid oxidizer and liquid fuel orifices in novel and nonobvious arrangements. In some embodiments, the injector interface includes a plurality of triplet and quadlet injector sets, with the fluid designed to enter the thrust chamber at carefully designed angles that improve burn efficiency and reduce temperatures at the wall surfaces.

In some embodiments, the fluid passages are designed to also reduce the impact of pressure waves that are an inherent byproduct of the fuel combustion used to generate thrust. For example, the fluid passages may be designed to branch off into smaller passages at staggered depths, rather than have all passages branch off at the same height or depth that may be seen in typical manufactured designs, due to the convenience in manufacturing that way. These asymmetries may create destructive interface when the pressure waves hit, that effectively raises the resonance frequency of the engine overall, thereby reducing the impact of the pressure waves.

Figure 2:
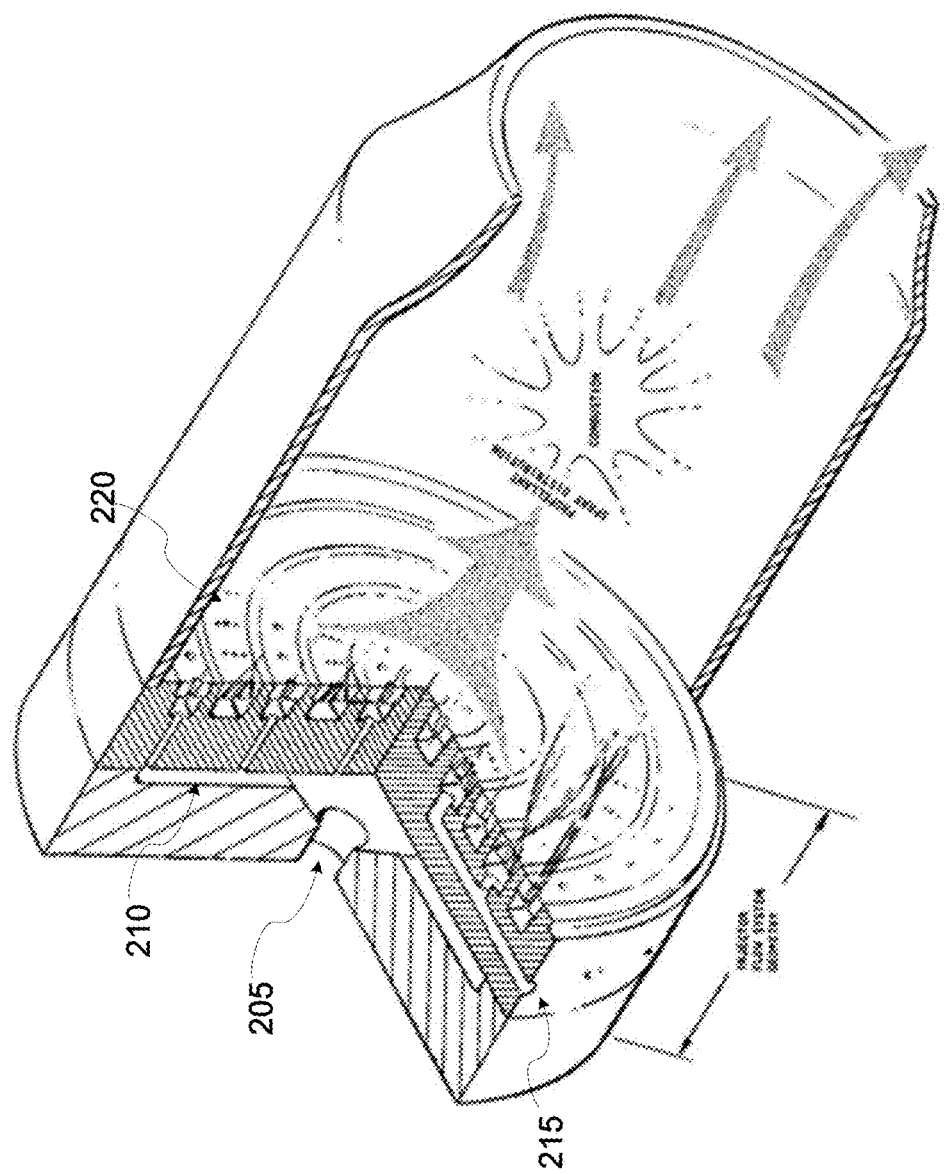
FIG. 2 shows an example of a typical injector flow system with collection chamber geometries.

FIGS. 1-2 and related descriptions provide descriptions of traditional thrust engine designs that serve as a point of comparison to highlight the novel and nonobvious features of the present disclosures.

FIG. 1 shows an illustration of an example of a typical injector plate collection chamber and orifice. There are two independent sets of passages leading into the injector plate: one for feeding fuel and another for feeding the liquid oxidizer. Shown is a side view cross section of an example injector plate with these two sets of passages. It can be seen that the directions of the passages form straight lines, and the connections are typically perpendicular to one another.

FIG. 2 shows an example of a typical injector flow system with collection chamber geometries. Liquid oxidizer enters the opening 205, which then fills a cylindrical chamber leading to channels forming three concentric rings 210 that exit at an injector plate 220. As shown, the concentric rings 210 exit the cylindrical chamber at right angles, meaning there is no gradual angle by which the liquid oxidizer exits.

This can create turbulence at the point of entry of the concentric rings 210, causing uneven flow into the combustion chamber through the injector plate 220. Similarly, the injector flow system of FIG. 2 includes a second series of channels 215 for a fuel injector path. The fuel may enter the channels 215 from a casing or sleeve surrounding the flow system. Here, the fuel then falls into two concentric rings interspersed between the three concentric rings 220 of the liquid oxidizer flow system. Still, the fuel enters these channels also at right angles, which also cause turbulence at the sharp and sudden turning points. Because of both channels having sharp angles, causing turbulent flow, the ignition between the fuel and oxidizer in the combustion chamber may occur very unevenly, creating unreliable and unstable burns. As shown, the fuel injector orifices are simple in design, yet still very difficult to manufacture. All the while, the designs are not optimal, as the fuel is likely to be injected at uneven rates or pressures, depending on stochastic movement for how the fuel would travel on top of the fuel injector plate before falling into the injector orifices.

Consistent with the examples shown in FIGS. 1 and 2, a typical injector would consist of a dome for distributing cryogenic or non-cryogenic oxidizers to the oxidizer orifices of the injector. Turbulence within the dome can yield unexpected flow to the numerous oxidizer orifices of the injector.

Fuel manifolds in a standard injector rely on collection chambers for pressure equalization in order to simplify flow calculations and reduce manufacturing costs. The result is rectangular channels with orifice feed channels extending perpendicular. Since collection chamber inlets do not follow the symmetry of the collection chamber itself, turbulence causes pressure drops within the chamber which also lead to nonuniform flow to the orifices.

In addition, standard manifolds are susceptible to combustion instabilities due to their resonant frequencies. As a result, collection chamber manifolds deliver positive feedback, increasing the intensity of the instability.

Typically, common element patterns are chosen and arranged for ease of manifolding and manufacturing, not to optimize propellant mixing and performance.

Aspects of the present disclosure provide an engine that is designed and manufactured in ways that address any and all of these issues found in typical engine design and manufacturing.

As previously mentioned, aspects of the present disclosure include branching fluid passages that reduce turbulent flow and generate evenly distributed fluid pressure as the fluids branch off into the different passages. In some embodiments, the branching passages may be subdivided into two sets: the branching passages for the liquid fuel and the branching passages for the liquid oxidizer. In some embodiments, the two sets of passages are carefully designed in an elegant yet extremely intricate manner that is optimized for proper fluid flow and maximal burn efficiency. The ends of all of the passages meet at the injector interface, which dispense the liquids into the combustion chamber for ignition. Generally, these designs are achieved through additive manufacturing, and would be extremely difficult, if not impossible, to be manufactured using traditional techniques.

Figure 3:
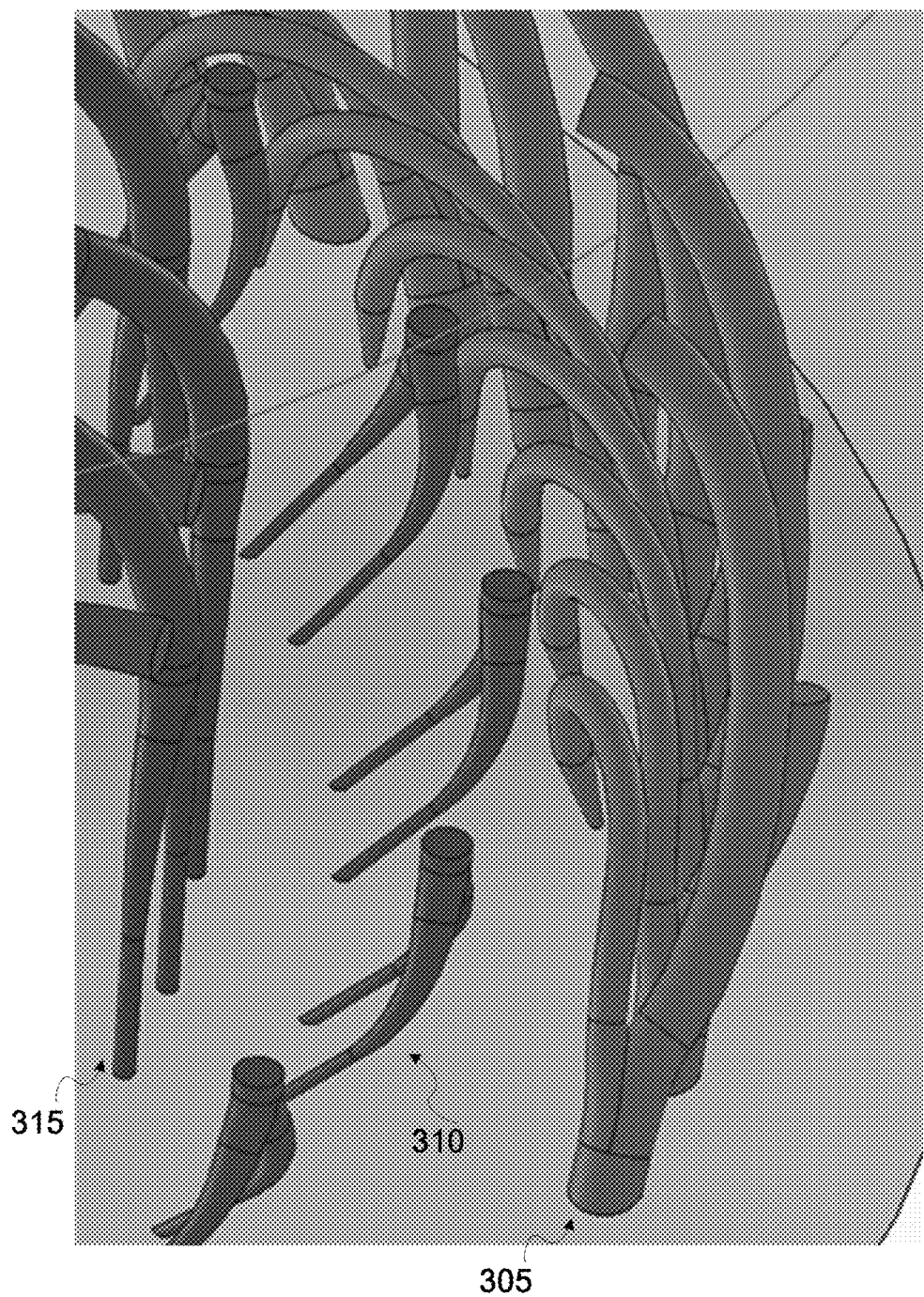
FIGS. 3 and 4 show simulation schematics of portions of the fluid passages, according to some embodiments.
Figure 4:
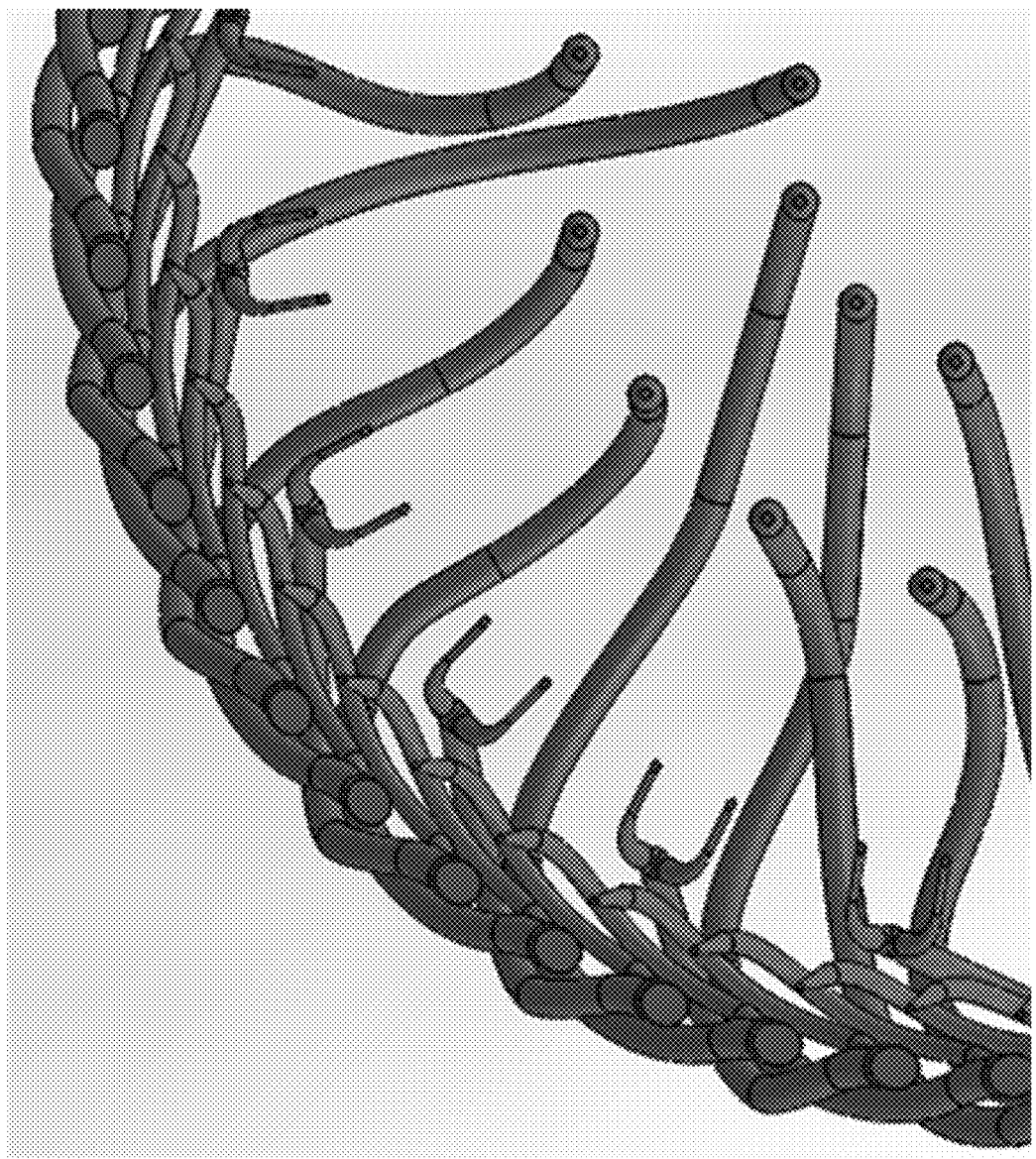

Referring to FIGS. 3 and 4, simulation schematics of portions of the fluid passages are shown, according to some embodiments. The schematics shown throughout this disclosure reveal the channels of the fractal fluid passages, according to some embodiments. In order to illustrate these passages, not shown are all the material filled in between each of the channels, though upon actual manufacture and implementation, the channels would be surrounding by the solid material filling in between the channels. In other words, the spaces between the illustrated channels are transparent for visual purposes, but in reality would have at least a portion actually filled in. Also, in some of the illustrations herein, for illustration purposes, portions of the passages may be cut off and not shown, though upon actual manufacture and implementation, the channels would smoothly connect to other portions of channels. The drawings herein may individually reveal just portions of a larger series of fractal fluid passages, and the totality of some combination of the drawings may therefore be used to provide a whole picture, when viewed in the collective.

For example, shown in FIG. 3 are portions of the injector passages that flow from and connect to the ends of regenerative cooling channels. In some embodiments, the lighter shaded passages 305 flow from and connect to the regenerative cooling channels that supply liquid fuel. The middle passages 310 featuring branching pairs are portions of passages that connect to other passages of the regenerative cooling channels. The darker shaded passages 315 flow down to supply liquid oxidizer, according to some embodiments. As shown in FIG. 3, some of the injector passages of the cooling channels 305 branch off, flow up, and then curve quickly—though still smoothly—downward. These passages may be positioned to inject part of the liquid fuel toward the edges of the combustion chamber, to provide a cooling effect to the wall surfaces and act as a film/boundary layer for the wall surfaces. As shown, these orifices are angled inward, back toward the wall surfaces. These branches will be described in more detail, below.

Referring to FIG. 4, shown here are additional portions of the regenerative cooling channels that feed into the orifices of the injector interface. This view is from the perspective of looking up from the bottom of the passages. The longer tubes extended toward the center of the circular injector interface would connect to branching pairs or triplets of orifices, according to some embodiments. These will be described in more detail, below.

In general, and in some embodiments, branching passages fed by the regenerative cooling passages feed the fuel orifices of the injector. Each regenerative cooling passageway feeds one film/boundary layer cooling orifice and one or more injector elements orifices. Proper area ratios are maintained to ensure that the proper mass flows reach each orifice. Passage shape is smooth to reduce turbulent head loss. Passage trajectories deliver fuel to the orifices along the most efficient route while avoiding liquid oxygen passages. These passages are designed using novel design methods, according to some embodiments.

In some embodiments, the pressure drop through the fuel injector passages is minimal at ~50 psi, as this comes from the acceleration of the flow. This occurs near the orifice exit where the passages converge to the orifice. A minimal pressure drop helps to reduce the total feed pressure required to drive fuel through the engine.

In some embodiments, pressure waves created from injector or combustion instabilities which attempt to propagate upward through the fuel passages will not affect the flow of other orifices in close proximity to produce feedback instabilities. The independently fed orifices prevent the interaction of pressure waves that would occur within a traditional manifold. In order for pressure waves propagating through one or more passages to interact, the waves must be very high in amplitude to pass through the regenerative cooling and into the diverter. If a wave should reach the diverter, the slight path length difference between the injector passages will yield out-of-phase pressure waves, which will interfere destructively.

FIGS. 5A-11 describe various aspects of the liquid oxidizer fractal fluid passages, according to some embodiments. Fractal branching fluid passages enable the transport of a fluid from a concentrated source to a larger surface area rapidly and without turbulent head loss. Branched fluid passages geometrically inhibit the propagation of potentially damaging combustion instabilities and pressure waves. In particular, the branched passages that contain some asymmetries (see e.g., FIGS. 5B, 9) in their shapes can disrupt the pressure waves, thereby creating a high resonant frequency. Example asymmetries can include slightly varying shapes, curves, positions, bumps, or angles in each of the branches relative to their neighbors and relative to the branch that would be positioned on the "mirror image" side of the fractal structure. Their structure possesses a high resonant frequency which prevents the resonance of undesirable waves which are typically present a much lower frequencies. Compare this to conventional designs with elegant-looking solutions but therefore having perfectly symmetrical designs. These have much lower resonant frequencies. Avoiding injector-combustion resonance is critical: for maintaining efficiency, ensuring that unstable waveform do not propagate upstream to tanks and other feed system components, where they may resonate, and for ensuring and ideal fuel/oxidizer mixture ratio and combustion efficiency over a wide range of throttling flows.

Figure 5A:
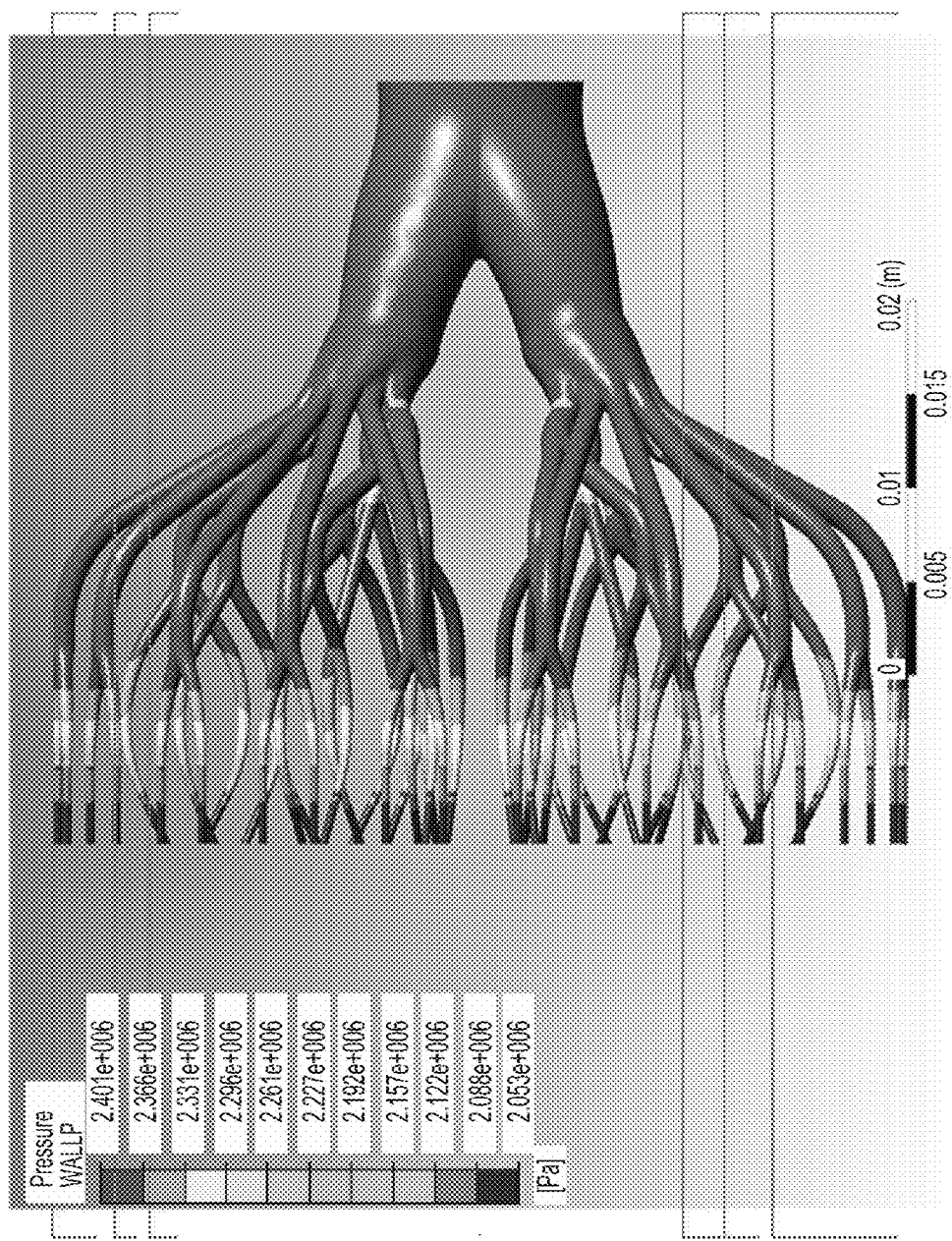
FIG. 5A is a side view of the main portions of fractal fluid passages to supply liquid oxidizer to an injector interface, according to some embodiments.

Shown in FIG. 5A is a side view of the main portions of fractal fluid passages to supply liquid oxidizer to the injector interface, according to some embodiments. According to the shaded key, the sizes of the passages are designed to provide a roughly equal amount of pressure drop in each passage at roughly the same distance from the injector interface, as shown by the shaded regions of the overall branching structure. In addition, it can be seen that the pressure of the fluid upon exiting the orifices are substantially uniform. Furthermore, other than narrowing or widening the channels as they approach the orifices, the remaining passages throughout the bulk of the structure provides substantially uniform pressure drop throughout, as indicated by the lack of color gradient in the bulk of the structure. In other cases, the pressure drop does not even change toward the ends at the orifices, as it is evident the channels at the ends of the branches can be maintained with constant cross-sectional area all the way down.

Branched passages maintain a relatively low fluid velocity while distributing fluid over an increased surface area. Fluid velocity is only permitted to increase at the passages final tier where the passages converge in order to accelerate the fluid through the orifice. Fractal branching mimics the biological distributions of fluids found in tree roots, cardiovascular and pulmonary systems, as well as being found in many other natural environments. Branched passages are capable of maintaining stability over a far greater range of initial and boundary conditions when compared to traditional fluid feed systems. These passages are designed to produce no turbulent pressure drop. Fractal passages are easily optimized for a variety of injector or fluid transmission schemes. They can be used to feed an arbitrary arrangement of fluid elements.

Figure 5B:
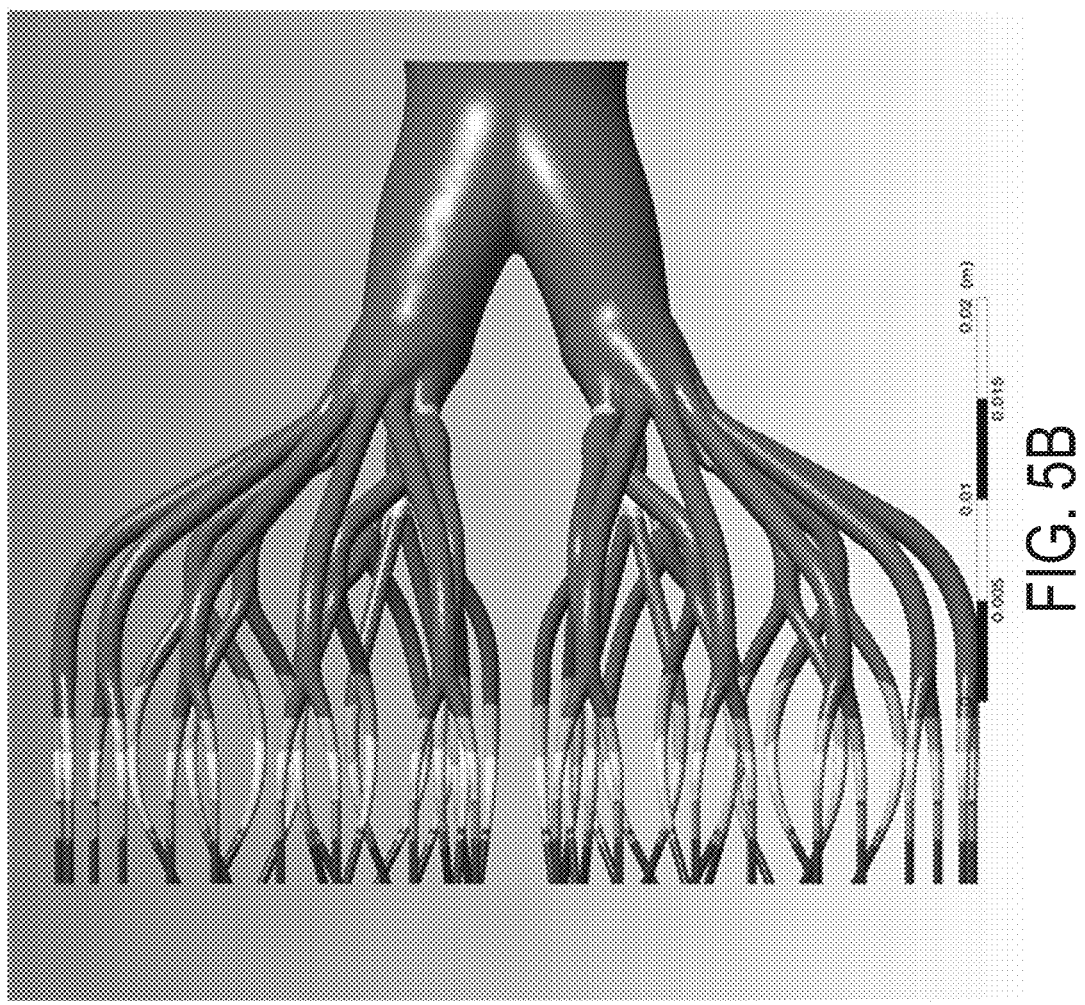
FIG. 5B shows the main portion of the fractal fluid passages but without the indications of the changes in pressure, in order to more clearly show the different branches and their varying depths, according to this side view

FIG. 5B shows the main portion of the fractal fluid passages but without the indications of the changes in pressure, in order to more clearly show the different branches and their varying depths, according to this side view. As shown, based on the side view, some branches extend forward, while others fall backward. As will be shown in further drawings, the branches may be spaced about to fill a cylindrical volume, and the orifices may be designed to end at an injector plate of uniform depth.

Figure 6A:
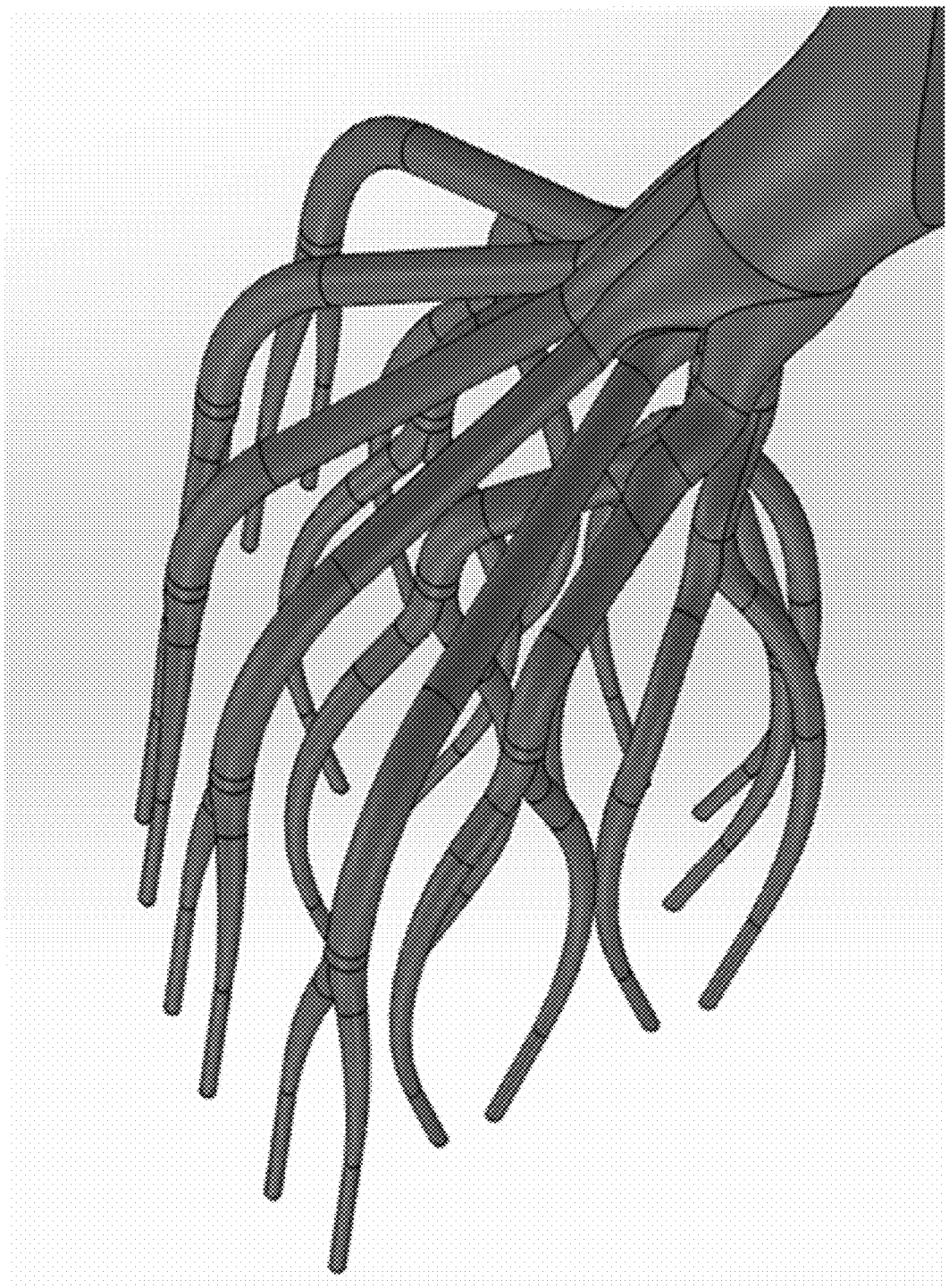
FIG. 6A shows a simulation rendering of a quarter armature of the liquid oxidizer passages, according to some embodiments.

Referring to FIG. 6A, a simulation rendering of a quarter armature of the liquid oxidizer passages is shown, according to some embodiments. It can be seen that the main branch divides itself into many multiple smaller branches, and from there, the smaller branches further subdivide one more time. The placement of the angles and subdivisions are purposely designed so as to reach the designated orifice position along the injector interface while providing even pressure drop, minimal turbulent flow and high pressure wave resistance. These constraints result in the branching patterns as shown, according to some embodiments. As shown, this drawing includes a series of lines running orthogonal to the direction of fluid flow. These lines represent changes in the geometry of the volumes used to define the shapes of the channels. As shown, some of the lines are spaced closely together, indicating that the geometries change quickly in those spaces. In others, the lines are spaced further apart, indicating that there are longer sections of the channels that can be defined by a single geometry, such as a longer tube with a single angle defining the curvature over that length. These lines, which are not necessarily present in the actual apparatus as implemented, may be present in the simulated design that is used to help construct a software version of the apparatus, which is then converted to a CAD file for use in manufacturing using additive manufacturing techniques, according to some embodiments. Alternatively, the lines may help define distinct polygons that may be pieced together to construct the channels of a fractal fluid passage design.

Figure 6B:
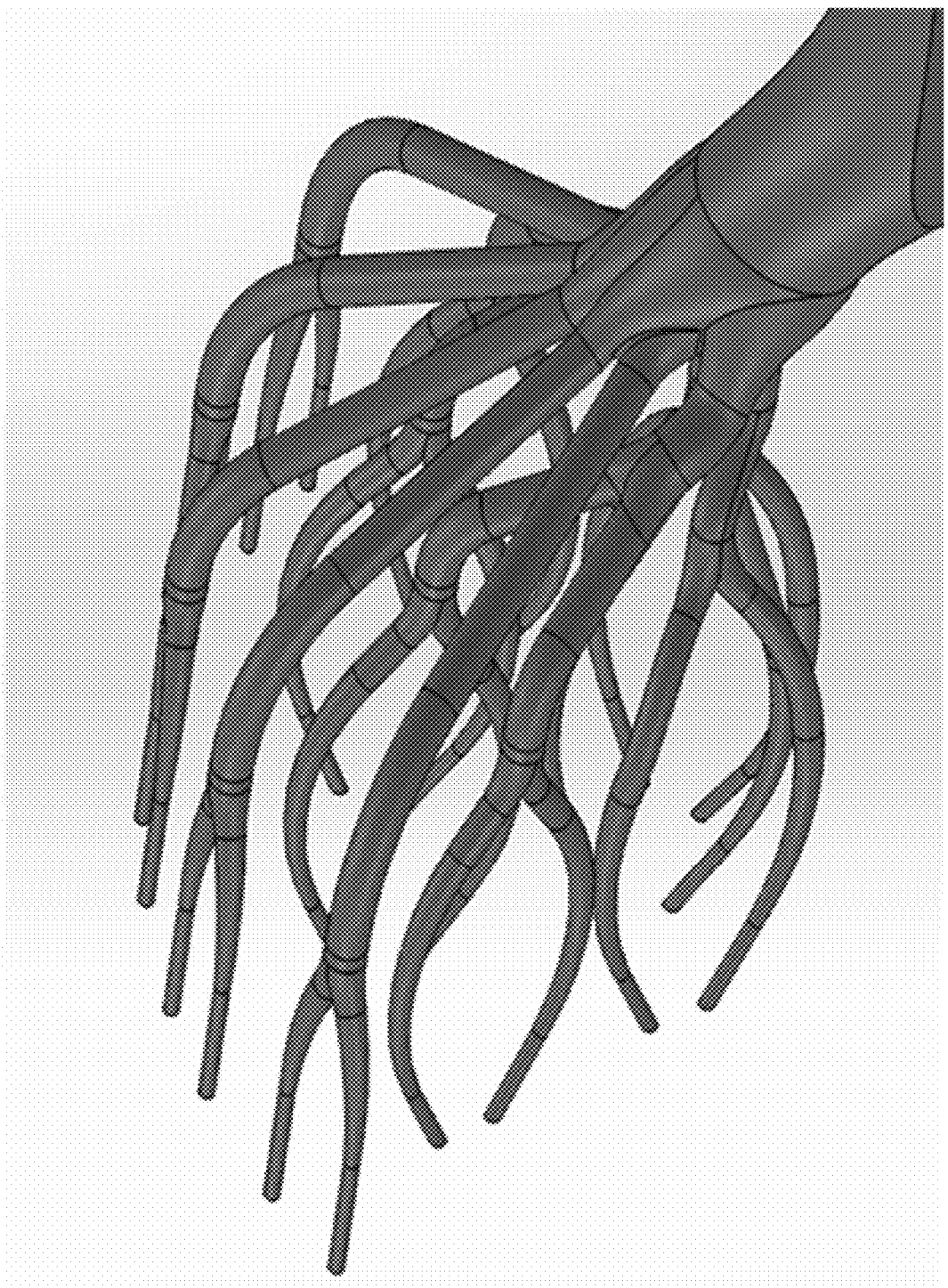
FIG. 6B shows a cleaner view of the quarter armature branching, without the dividing lines.

FIG. 6B shows a cleaner view of the quarter armature branching, without the dividing lines. As mentioned, actual additively manufactured smooth fractal passages would not include any defining lines, and would be defined more by very smooth channels, or at least channels that gradually change direction. Apparatuses with coarse fractal channels are possible, in the sense that the passages may not be completely smoothly refined inside.

Figure 7:
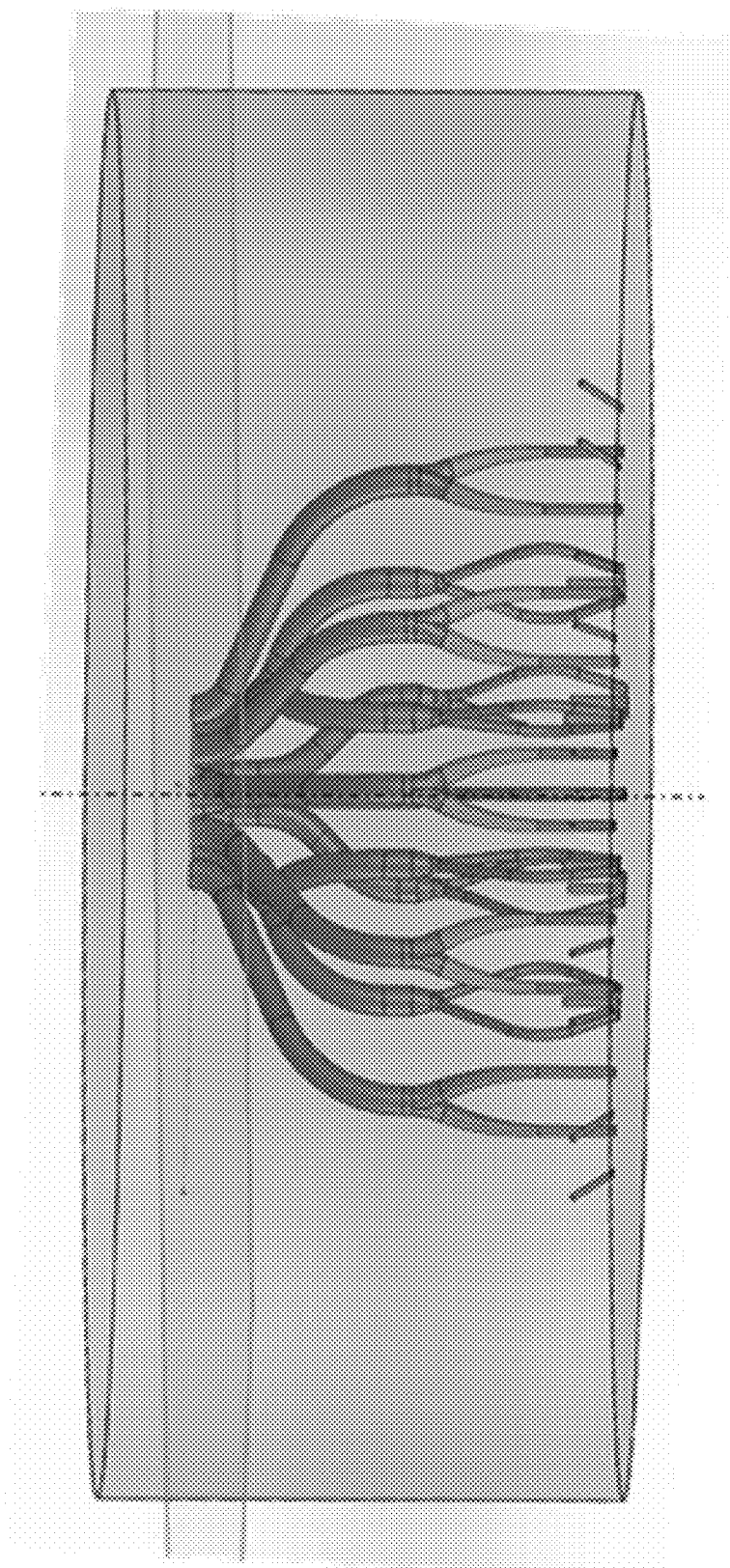
FIG. 7 shows another example fluid passage design for the liquid oxidizer, according to some embodiments.

FIG. 7 shows another example fluid passage design for the liquid oxidizer, according to some embodiments. Also shown are the end portions of the fuel orifices, placed at the injector interface at more acute angles. These will be discussed in more detail, below.

Figure 8:
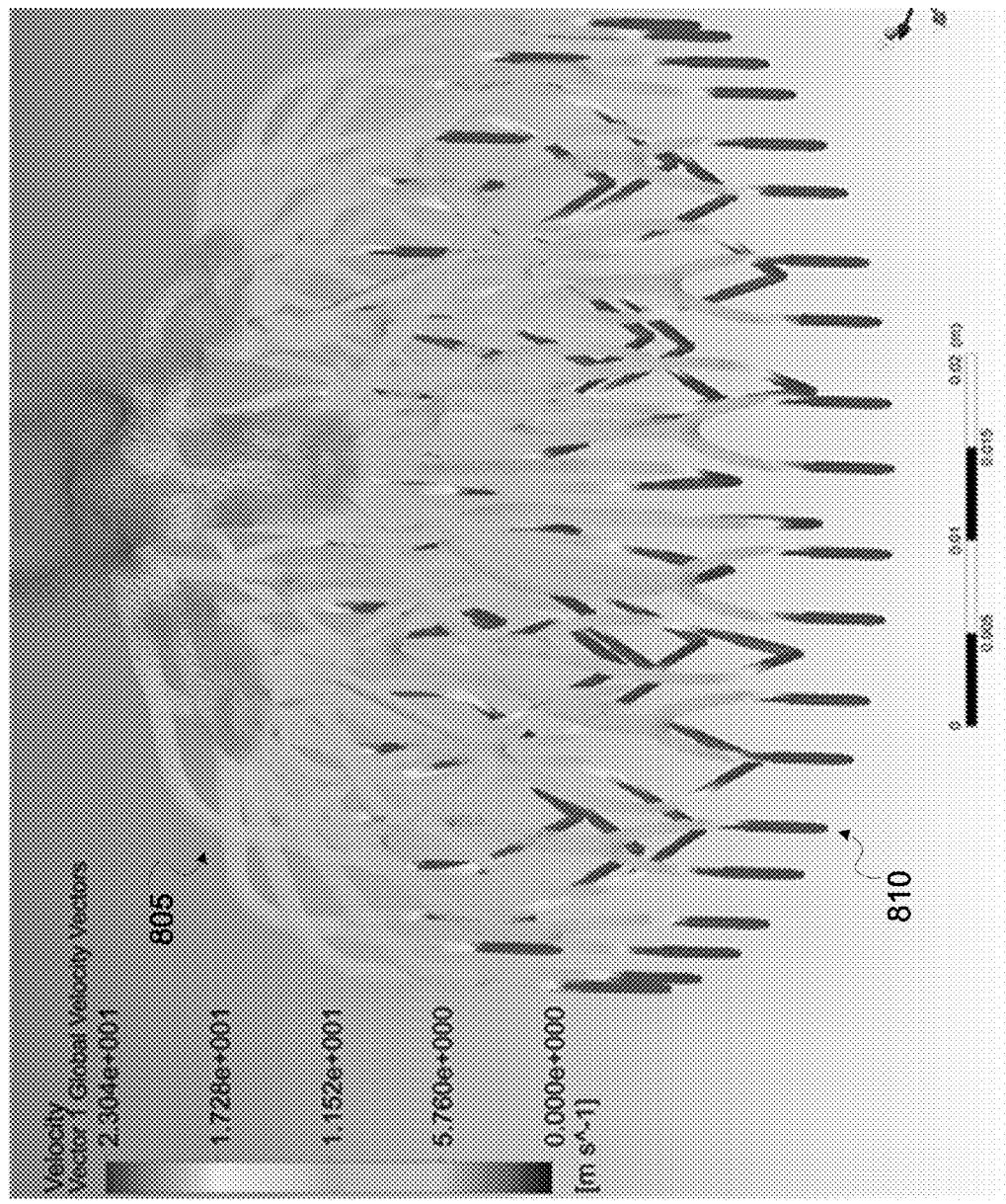
FIG. 8 shows a schematic of the liquid oxidizer fluid passages shaded according to fluid velocity, according to some embodiments.

FIG. 8 shows a schematic of the liquid oxidizer fluid passages shaded according to fluid velocity, according to some embodiments. As shown, most of the passages maintain a relatively constant and low velocity throughout, according to the lighter shaded regions 805 that correspond to the lighter shaded portion of the key, showing velocity of the liquid. The bottom portions of the passages 810 show a darker shade, corresponding to a higher velocity as described in the upper range of the key. As shown, the higher velocity portions are consistently only at the bottom ends of each of the passages, which is to help ensure ejection of the liquid through the injector orifices. Significantly, the velocity of the fluid exiting the orifices may be substantially uniform, regardless of what the velocity is relative to the fluid while traveling through the passages. In addition, in some embodiments, the velocity of the fluid traveling within the channels may be substantially uniform throughout, and change only when nearing the orifices. This is possible because of the smooth curvature of the passages even as they transition from one branch into multiple branches.

Figure 9:
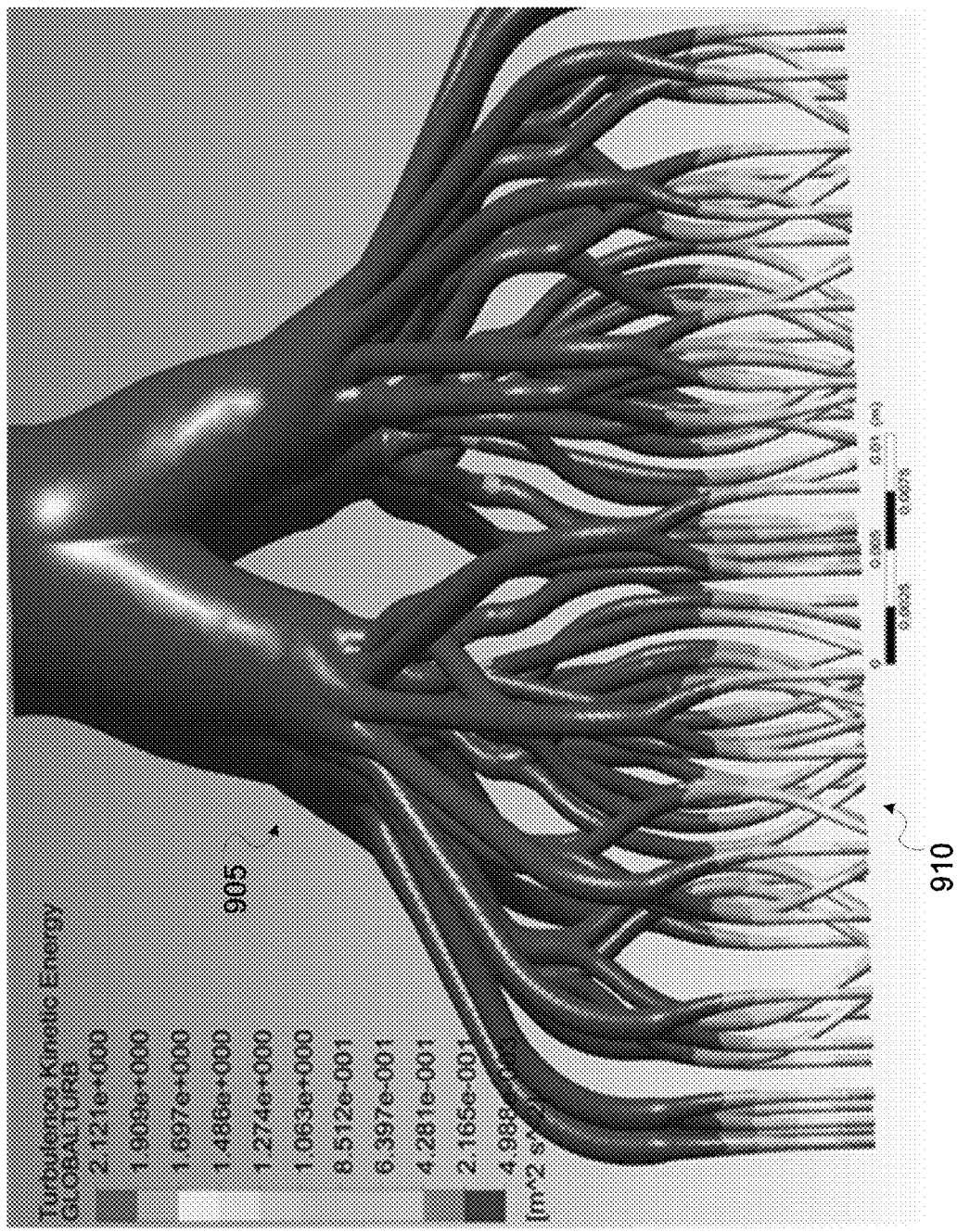
FIG. 9 shows a schematic of the liquid oxidizer fluid passages shaded according to turbulent kinetic energy, according to some embodiments.

FIG. 9 shows a schematic of the liquid oxidizer fluid passages shaded according to turbulent kinetic energy, according to some embodiments. As shown, most of the passages maintain a relatively constant and low turbulence throughout, according to the darkest shaded regions 905 that correspond to the darkest shaded portion at the bottom of the key, showing turbulence kinetic energy. It is only at the bottom portions of the passages 910 where the turbulence increases, corresponding to a higher velocity as described in the upper range of the key.

Figure 10:
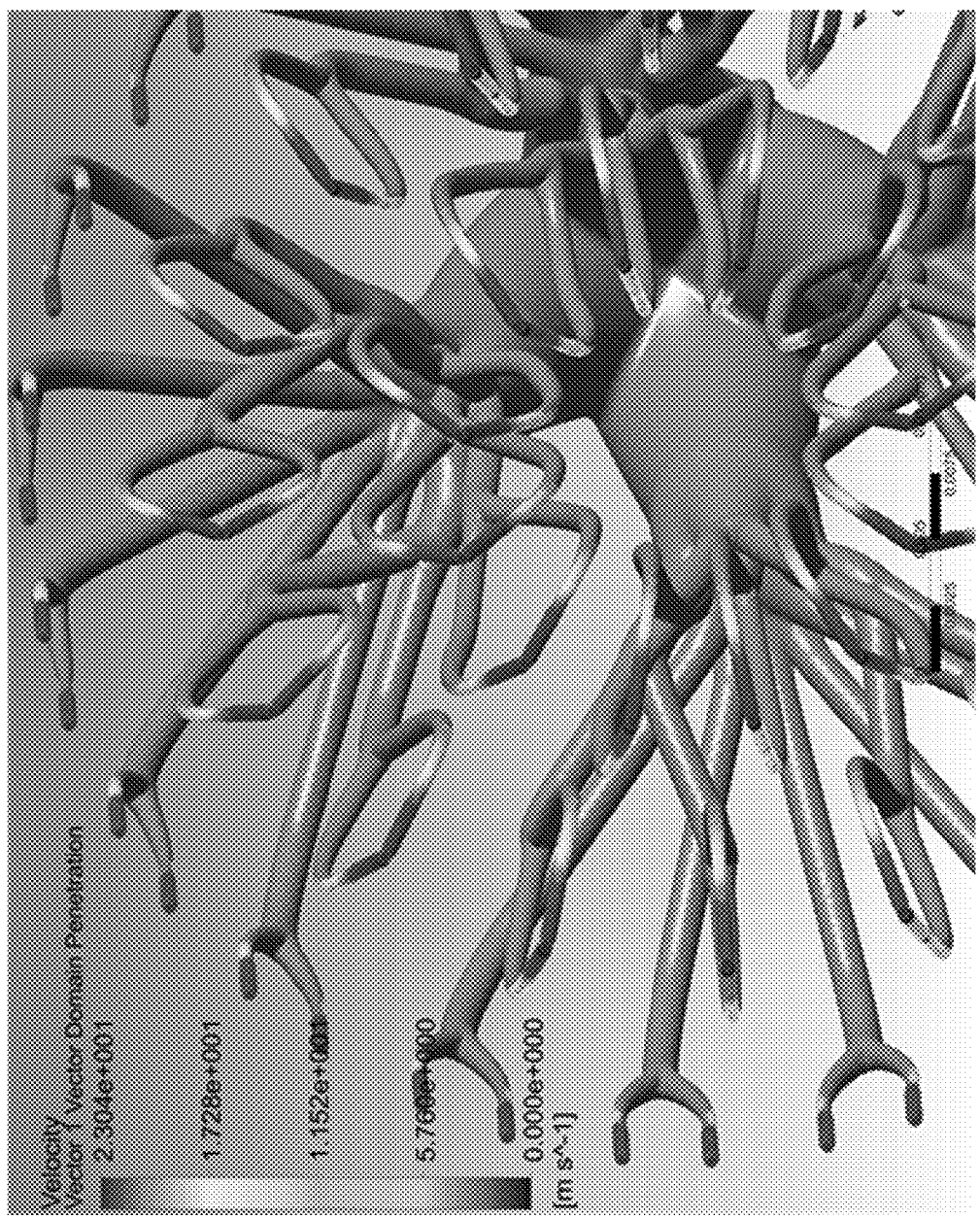
FIG. 10 shows a schematic of a different angle of the liquid oxidizer fluid passages shaded according to fluid velocity, according to some embodiments.

FIG. 10 shows a schematic of a different angle of the liquid oxidizer fluid passages shaded according to fluid velocity, according to some embodiments. This view shows how the orifices are angled in specific and varied directions. As shown, most of the passages maintain a relatively constant and low velocity throughout. The bottom ends (orifices) of the passages show the darkest shade, corresponding to a higher velocity as described in the upper range of the key. As shown, the higher velocity portions are consistently only at the bottom ends of each of the passages, which is to help ensure ejection of the liquid through the injector orifices.

Figure 11:
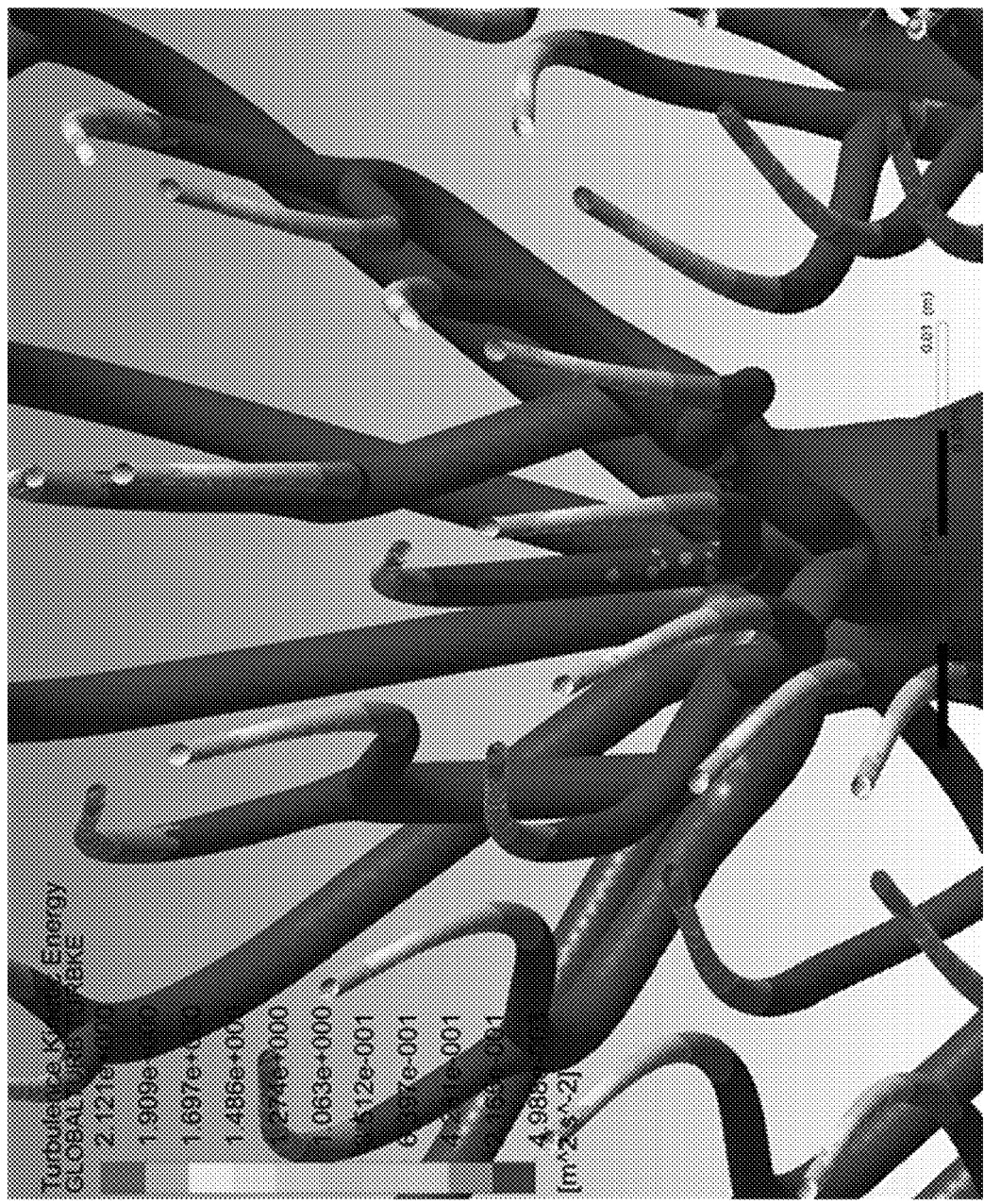
FIG. 11 shows a schematic of a different angle of the liquid oxidizer fluid passages shaded according to turbulent kinetic energy, according to some embodiments.

FIG. 11 shows a schematic of a different angle of the liquid oxidizer fluid passages shaded according to turbulent kinetic energy, according to some embodiments. This view shows an upside down angle of the orifices. As shown, most of the passages maintain a relatively constant and low turbulence throughout, according to the darkest shaded regions that correspond to the darkest shaded portion at the bottom of the key. It is only at the ends of the passages (orifices) where the turbulence increases, corresponding to a higher velocity as described in the upper range of the key. In other cases, the velocity throughout the passages does not change, even at the ends near the orifices. In general, the passages may be designed to achieve any desired amount of velocity, including any specific changes to velocity within the passages, and embodiments are not so limited.

The descriptions in FIGS. 8-11 provide evidence of an extremely stable system of passages. The high stability of these passages makes them well suited for: quenching combustion instabilities or other unstable fluid-transmissive waves, reacting flows high pressure and high flow situations, as well as environments where stable outflows are required despite intermittent or turbulent initial and boundary conditions.

Figure 12:
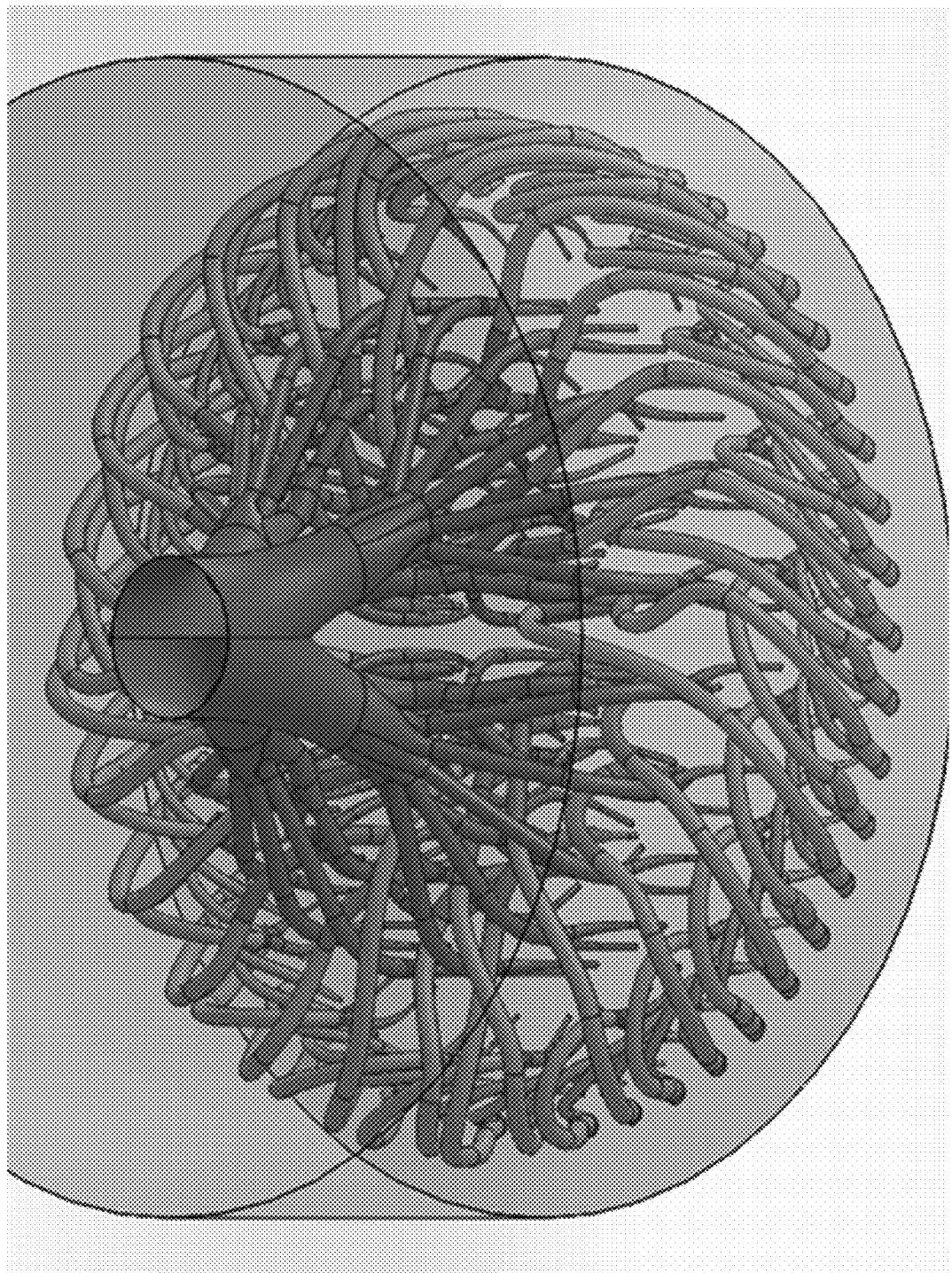
FIG. 12 shows a schematic combining both sets of the liquid fuel passages and the liquid oxidizer passages into the injector interface, according to some embodiments.

FIGS. 12-15 describe the combined system of passages of the liquid fuel and liquid oxidizer and how they intermingle into the injector interface. Referring to FIG. 12, shown is a schematic combining both sets of the liquid fuel passages and the liquid oxidizer passages into the injector interface, according to some embodiments. Shown is only a section of a larger apparatus that includes passages connecting to the tops and bottoms of the passages shown here. The outer ring of passages is the extension of the liquid fuel passages connected to the cooling channels that flow up the walls of the combustion chamber. As shown and previously described, a portion of the passages quickly turn down and inject the fuel on the edges of the inner chamber wall surfaces, to act as coolant. Also shown, other portions of these passages extend into various positions toward the center, intermingling with the passages of the liquid oxidizer, which is positioned in the center and shows an opening at the top that connects to the liquid oxidizer tank. The opening represents the inlet from which liquid oxidizer flows down and into the fractal fluid passages of the inner passages structure. It can be observed how intricate the formations of the passages are, all the while providing smooth, continuous flow that is highly stable.

In some embodiments, due to the cryogenic nature of the liquid oxidizer (typically LOX), minimizing the inlet to orifice passage length is prioritized. As a result, the fuel passages may be designed to accommodate this optimization. The minimum spacing between passages may be determined by the resolution of the apparatus used to create these passages using additive manufacturing, e.g., resolution of the 3D printer.

Figure 13:
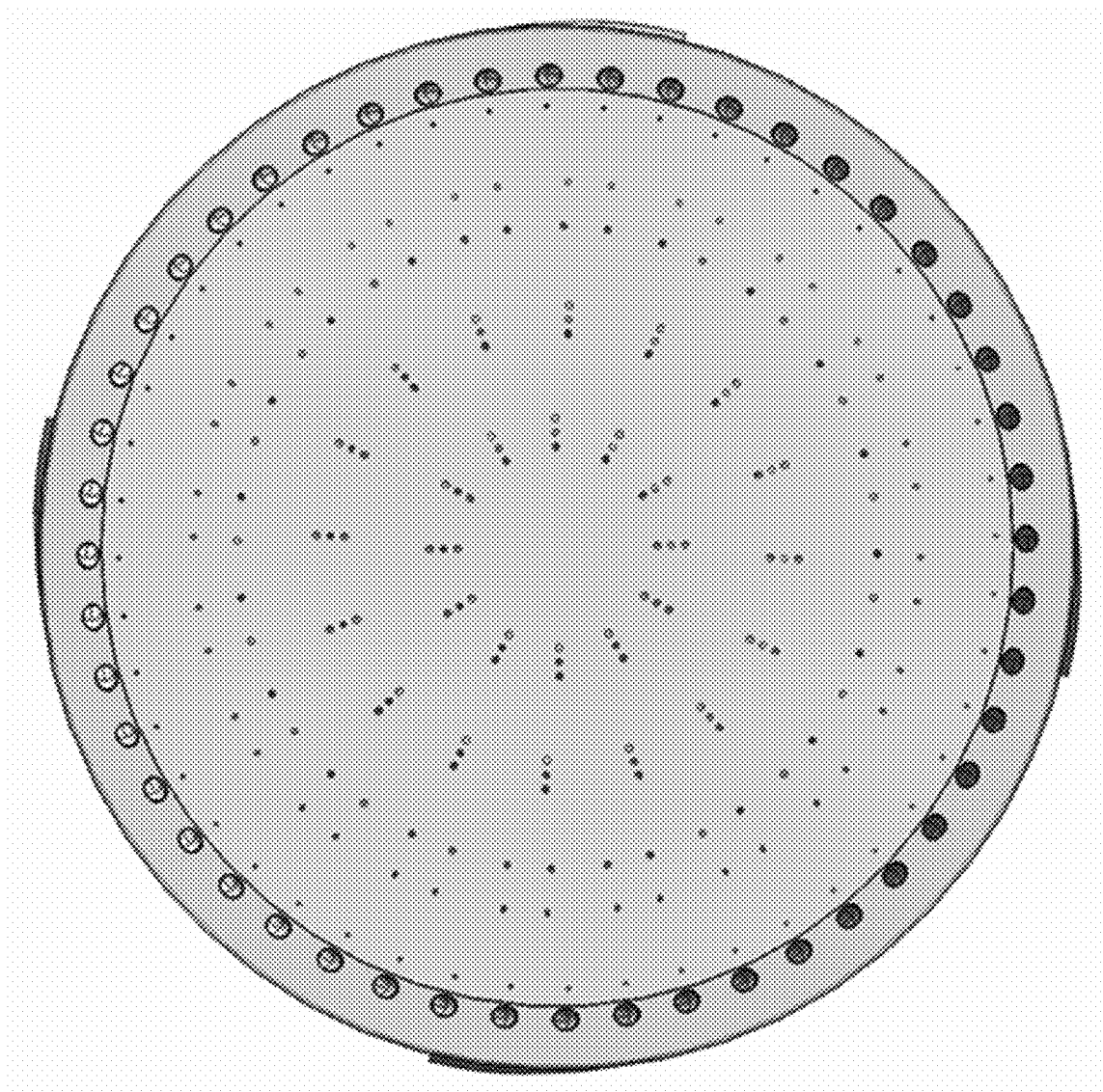
FIG. 13 shows the opposite side of the injector interface, showing the ultimate arrangement for how the orifices are positioned to inject liquid into the combustion chamber, according to some embodiments.

FIG. 13 shows the opposite side of the injector interface (see FIG. 12), showing the ultimate arrangement for how the orifices are positioned to inject liquid into the combustion chamber, according to some embodiments. The orifices of both the oxidizer and the liquid fuel may intermingle to be grouped into sets of triplets or quadlets (sometimes referred to as unlike doublets). The triplet includes two orifices from one set of fluid passages for delivering one type of liquid, and one orifice from a second set of fluid passages for delivering a second type of liquid. The quadlet or unlike doublet includes at least one orifice from the first set of fluid passages, and at least one orifice from the second set of fluid passages. Each triplet or quadlet is defined as an element. The element pattern's primary role is to efficiently distribute and atomize fuel in the combustion chamber, in this case. In order to accomplish the efficient mass flow distribution, a large number of orifices are required. FIG. 13 shows one example of an element pattern, though other patterns are possible and are within the scope of the present disclosures. The element pattern includes three different types of elements: triplets, quadlets, and shower heads.

In this example, triplets contain three orifices; two LOX and one liquid fuel (e.g., RP-1) in an oxidizer-fuel-oxidizer (OFO) pattern. In some embodiments, OFO is chosen because it provides a symmetrical element with no need to worry about varying momentum. In some embodiments, the triplets have an injection angle of 30° between oxidizer and fuel. The 30° provides enough of an intersection between fuel and oxidizer while still keeping the injection stream with a majority down chamber flow path. The triplet is selected for the center and majority of the injector plate because it provides steady, efficient combustion. This is due to the optimal mixture ratio of LOX/RP-1 being 2.56. This means that the orifices of the LOX and RP-1 are very similar in cross sectional area, resulting in efficient atomization because of similar particle size.

Figure 14:
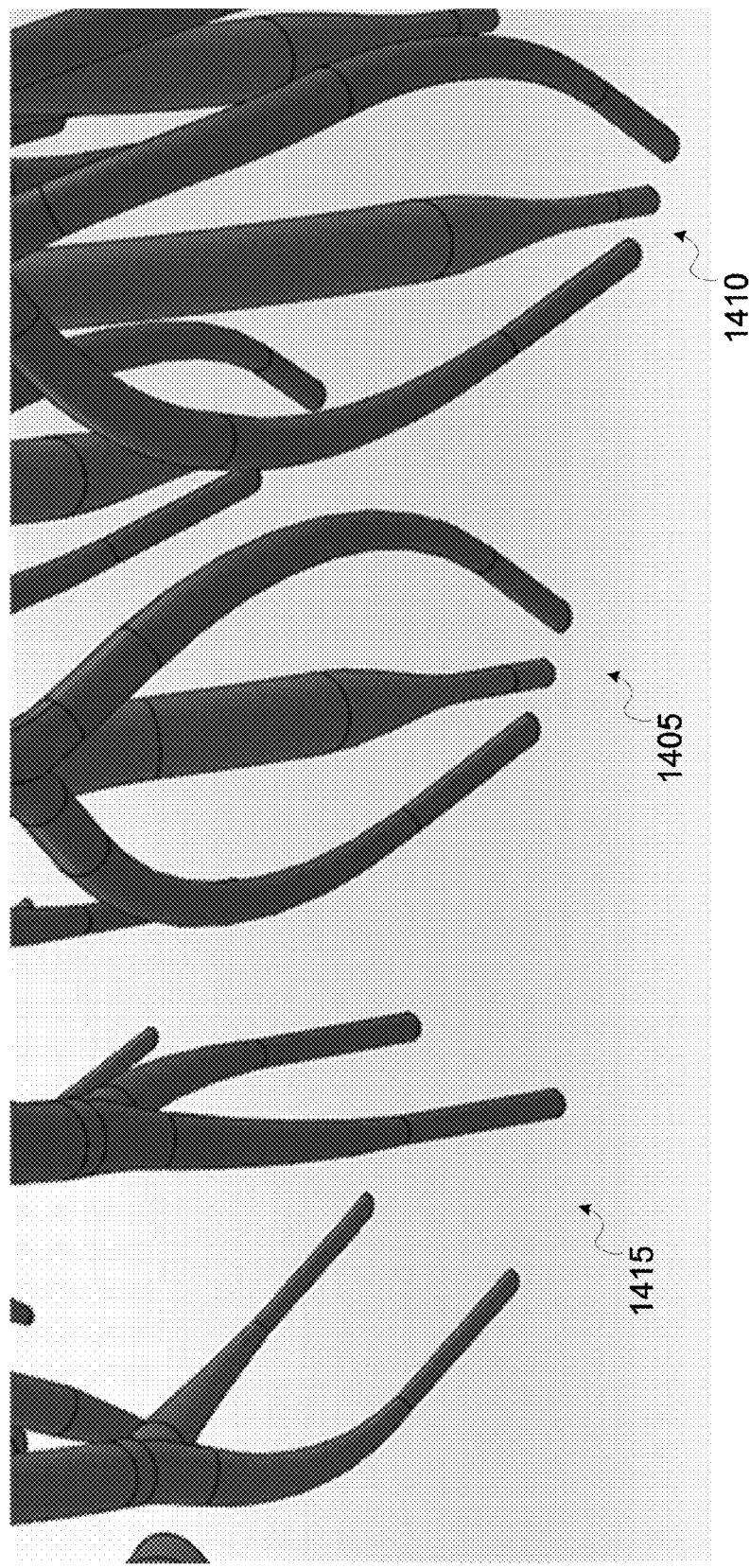
FIG. 14 shows a close up view of two triplet elements and one quadlet element.

In some embodiments, the quadlet is selected for the exterior areas in order to provide a fuel rich ring of combustion. The quadlet contains more RP-1 than the triplets resulting in a fuel rich flame. This creates a lower temperature profile near the walls to reduce melting. FIG. 14 shows a close up view of two triplet elements 1405 and 1410 and one quadlet element 1415.

Referring back to FIG. 13, the orifices arranged in a ring closest to the chamber wall may be defined as a showerhead element. The showerhead is comprised of individual fuel orifices. These are angled toward the wall and provide a layer of protection against the high temperatures of combustion. The fuel is assumed to not combust with the absence of an oxidizer. Once the liquid fuel has evaporated, it provides a subsonic layer of gas fuel. This element is consistent with the descriptions in the previous figures in how a portion of the liquid fuel is injected purposefully toward the edges of the combustion chamber and onto the wall surface.

Combustion instabilities are one of the main issues for injector plates. In order to maximize combustion efficiency, orifices are selected to be as small as possible. Traditionally, large baffles are used to stop resonating. However, the selection of three different types of elements helps to mitigate these combustion instabilities. Each element creates oscillations at a different frequency. By utilizing multiple elements the combustion instabilities are for all intents and purposes a non-issue. Therefore, baffles are not required.

Figure 15:
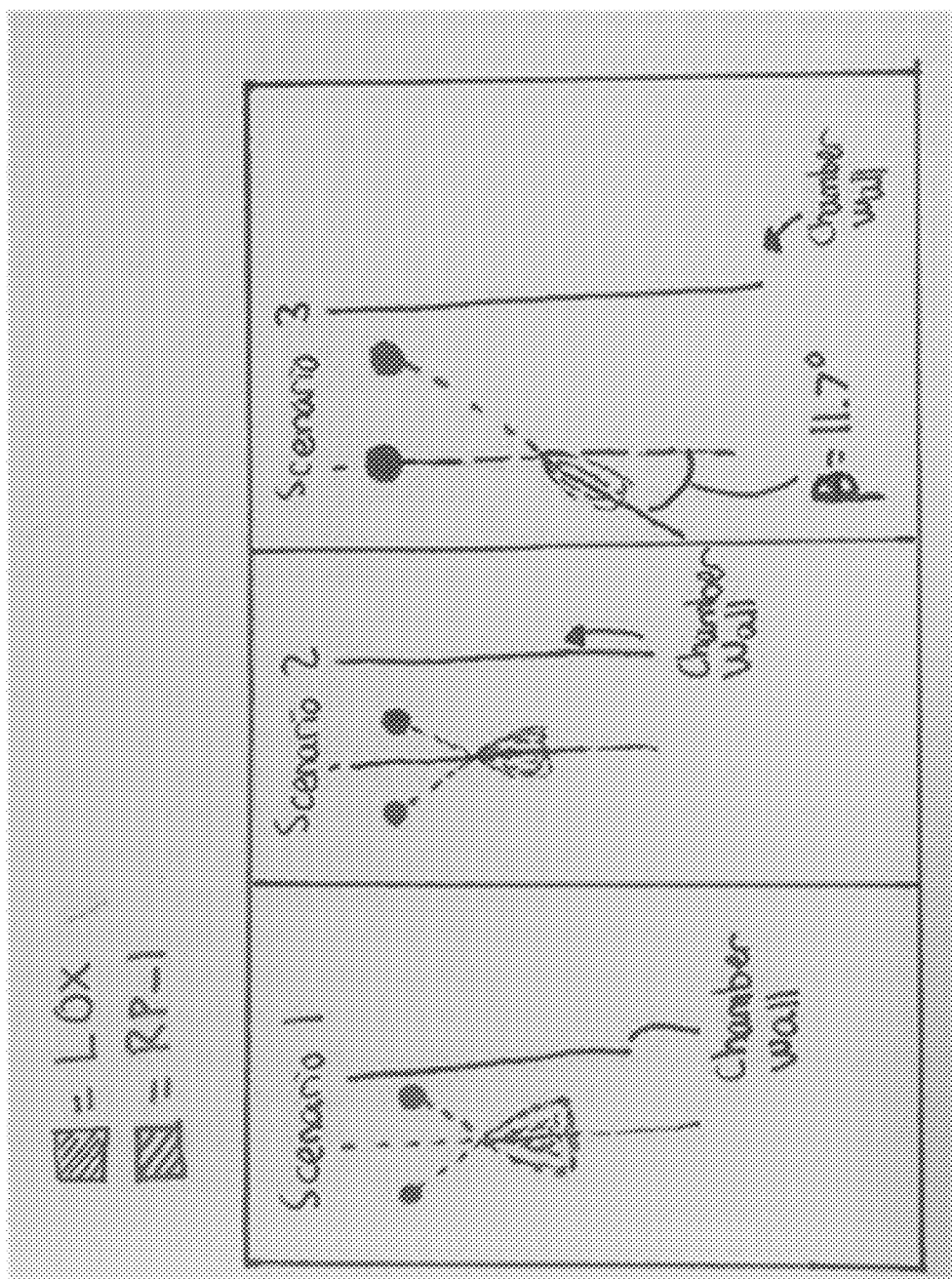
FIG. 15 shows three different scenarios for choices of arranging which type of liquid at which type of angle in the quadlet.

The injector contains a unique radially outward fuel rich gradient that helps to minimize wall melting and failure. As shown, there is a higher concentration of orifices toward the center that are designed to maximize fuel burn, while there is a lower concentration on the outer rings to reduce the chance of burn damage to the inner wall. This lowers the adiabatic flame temperature which inherently results in a lower temperature wall. Furthermore, because LOX creates a high temperature flame, it is important to note that the LOX orifices are located radially inward in the quadlets. This ensures that the walls are only being exposed to either fuel film cooling, or fuel rich flame. FIG. 15 shows three different scenarios for choices of arranging which type of liquid at which type of angle in the quadlet. Scenario 3 has been reasoned to be a more favorable arrangement, due to the closest orifice injecting liquid away from the chamber wall so as to reduce heat at the wall surface.

In general, embodiments include an injector interface having a combination of triplets and quadlets, and in some cases showerheads, may be arranged in any sort of combination according to design principles by those with skill in the art, and embodiments are not so limited.

Figure 16:
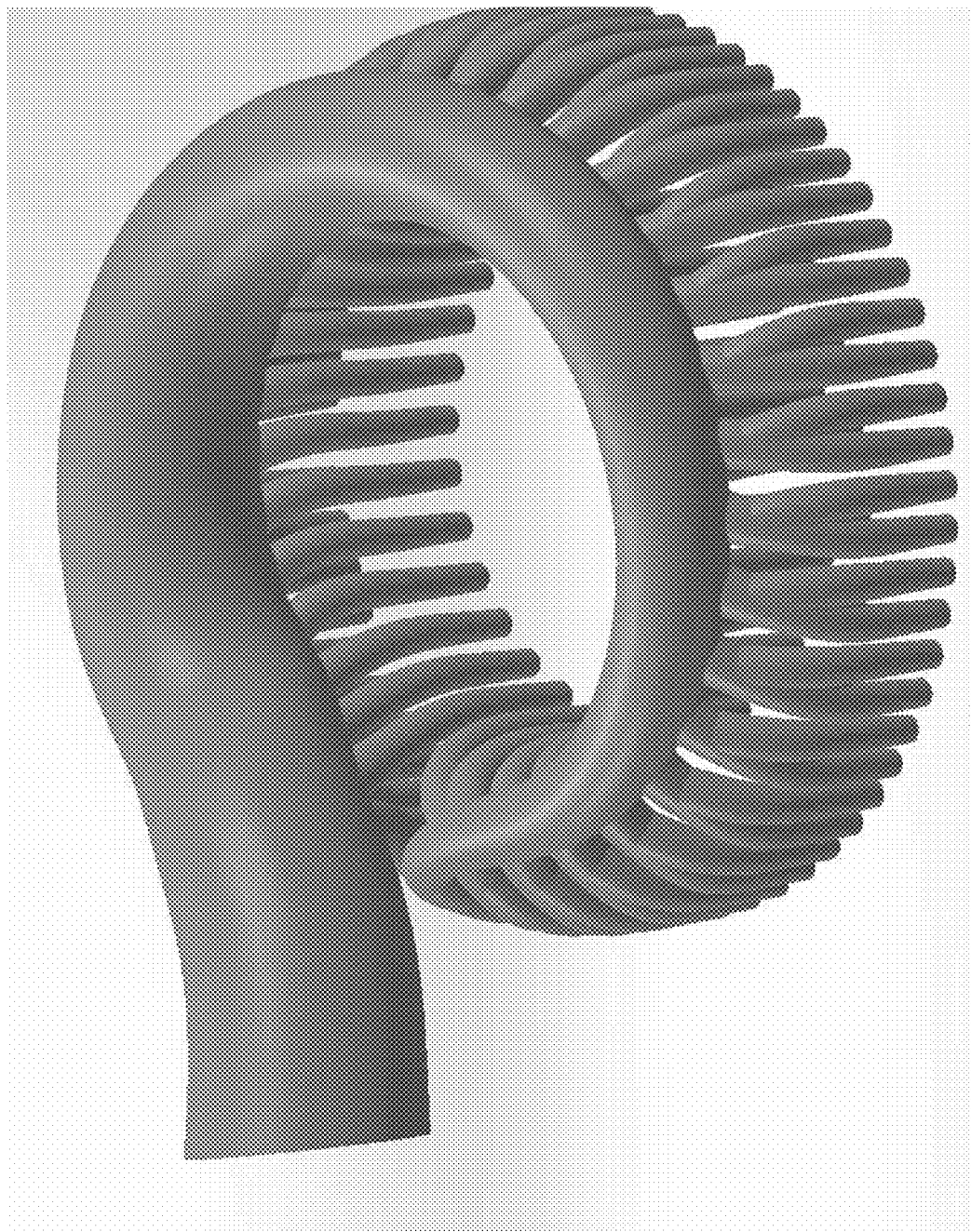
FIG. 16 shows a perspective view of an example of a decreasing radius annulus diverter design incorporated into the fractal fluid passages for the liquid oxidizer.

Referring to FIGS. 16-20, in some embodiments, a decreasing annulus fluid diverter may be employed to be included as part of the design for the fractal fluid passages leading to the injector orifices. General descriptions of a decreasing annulus fluid diverter are discussed in U.S. Provisional Application 62/382,722 ("STRUCTURAL HEAT EXCHANGER"), which is incorporated herein by reference in its entirety. The general concepts of that fluid diverter may be applied to feed the branching passages into the injector interface. A perspective view of an example of such a design is shown in FIG. 16. Here, the liquid oxidizer may be delivered initially through the large portion of the passage on the top left. Multiple fractal passages may connect to the diverter in series. The main channel may be arranged in a circular fashion, although in other cases this is not the case. As each of the fractal passages divert some of the fluid away from the main passage, the radius of the diverter progressively decreases, in proportion that compensates for the anticipated pressure drop due to the diverted fluid. In this way, the pressure drop throughout the diverter remains constant.

Figure 17:
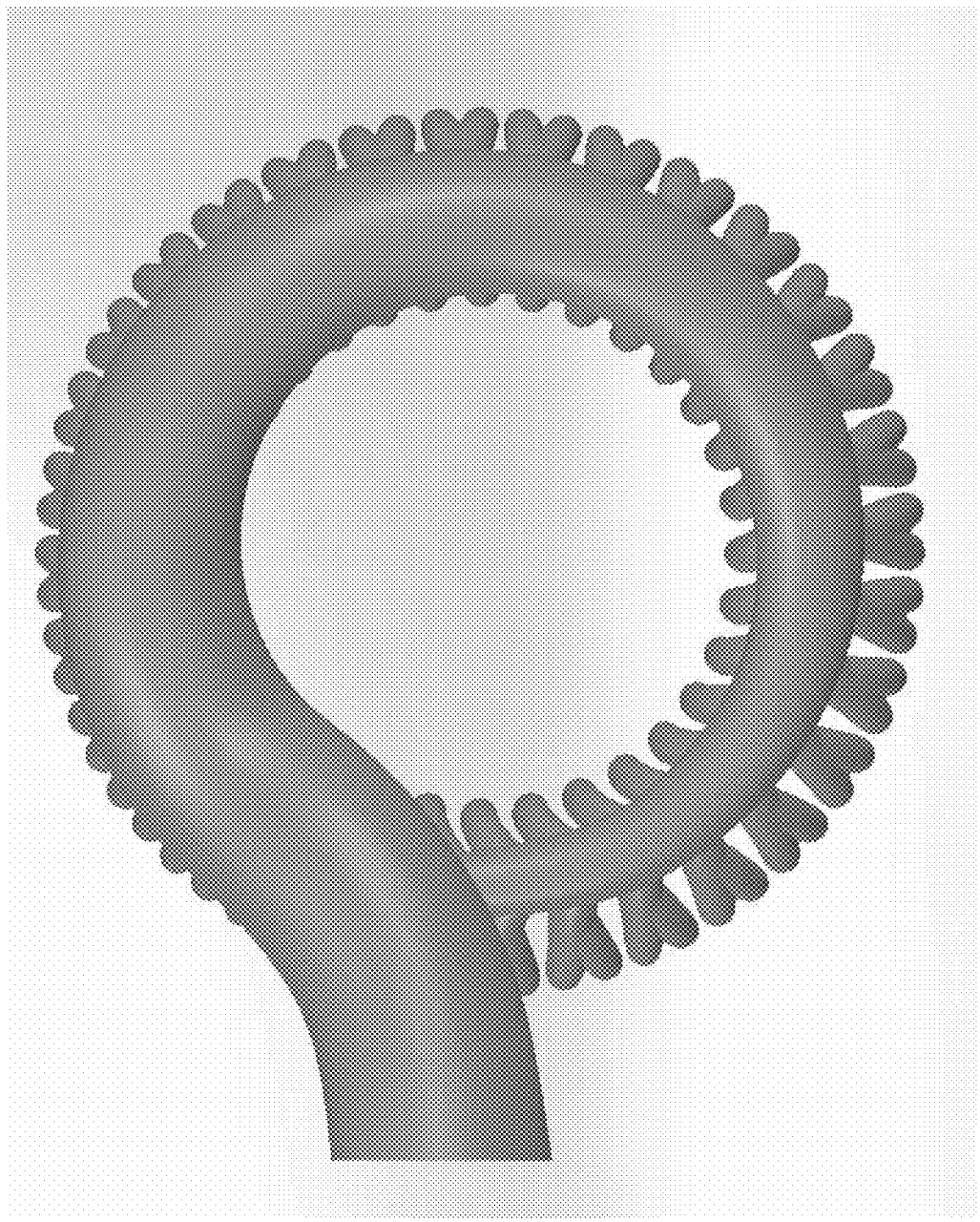
FIG. 17 shows a top-down view of the example fluid diverter employed in the liquid oxidizer fluid passages design.
Figure 18:
FIG. 18 shows a bottom-up view of the example fluid diverter employed in the liquid oxidizer fluid passages design.
Figure 19:
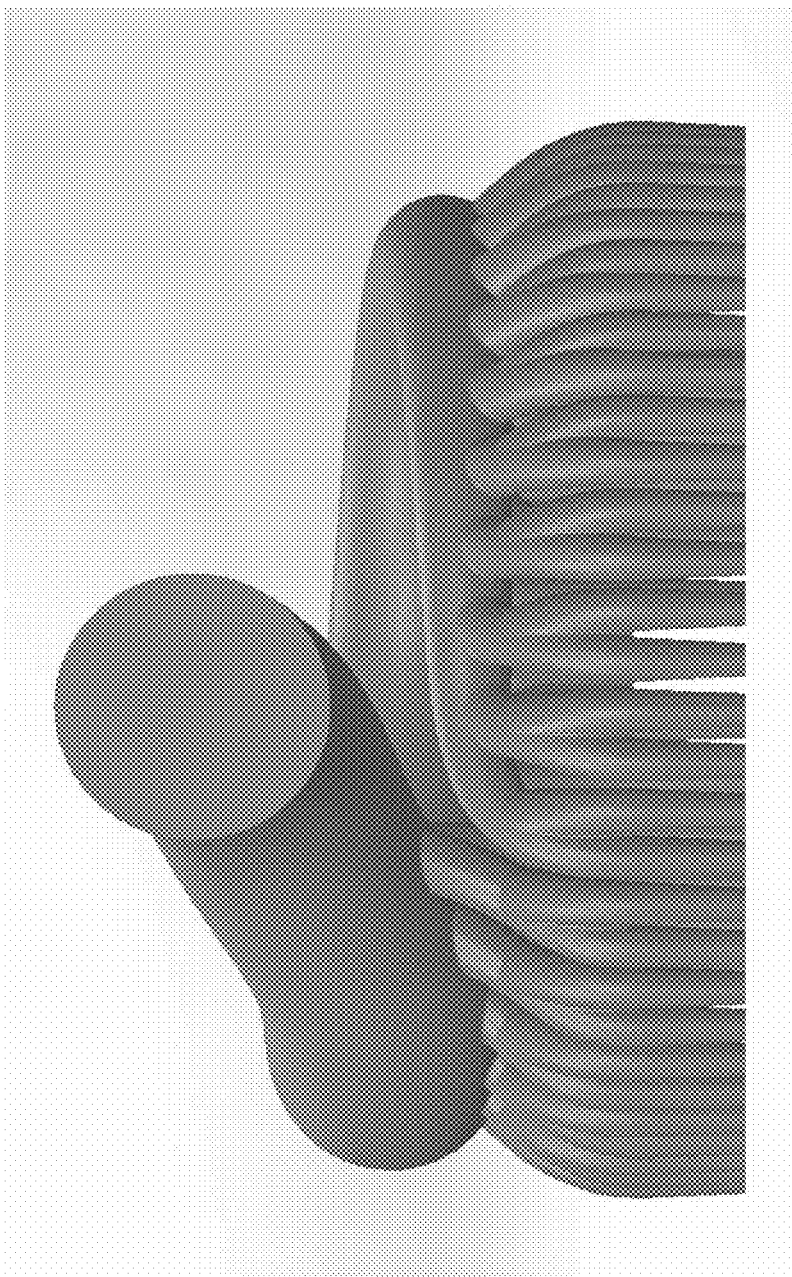
FIG. 19 shows one side view of a CAD rendering of the example fluid diverter employed in the liquid oxidizer fluid passages design.
Figure 20:
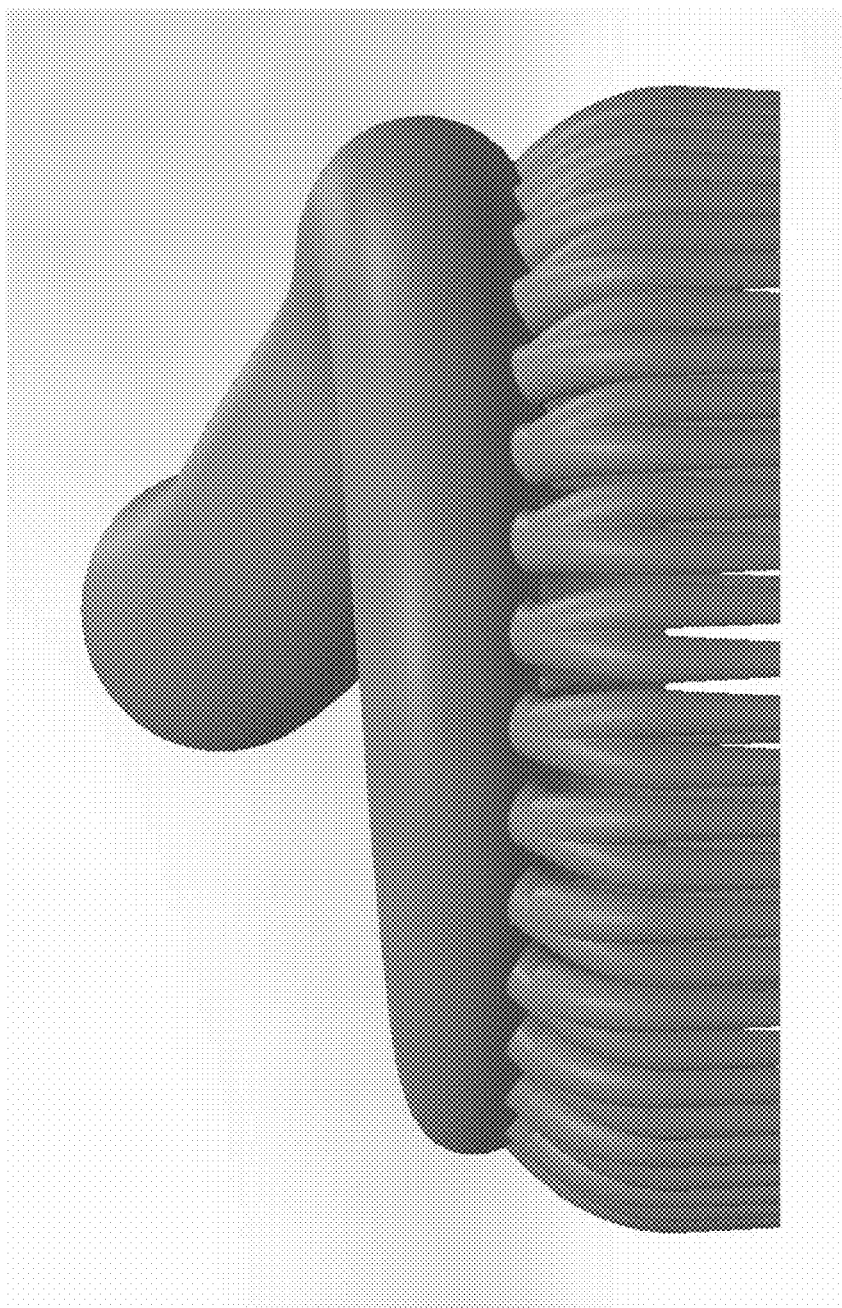
FIG. 20 shows an opposite side view of the CAD rendering from FIG. 19.

FIG. 17 shows a top-down view of the example fluid diverter employed in the liquid oxidizer fluid passages design. FIG. 18 shows a bottom-up view of the example fluid diverter employed in the liquid oxidizer fluid passages design. FIG. 19 shows one side view of a CAD rendering of the example fluid diverter employed in the liquid oxidizer fluid passages design. As shown, the main fluid passage is largest at the beginning, and becomes decreasingly smaller radially the farther along the fluid travels. It can be seen clearly here an example of how the fractal passages branch off from the main diverter channel. FIG. 20 shows an opposite side view of the CAD rendering from FIG. 19.

FIGS. 21-26 show another example of a decreasing annulus fluid diverter that may be employed to be included as part of the design for the fractal fluid passages leading to the injector orifices, according to some embodiments. In this case, each fluid passage from the decreasing annulus diverter leads to three injector orifices. This creates more asymmetry into the design, which increases stability and reduces the effects of pressure waves.

Figure 21:
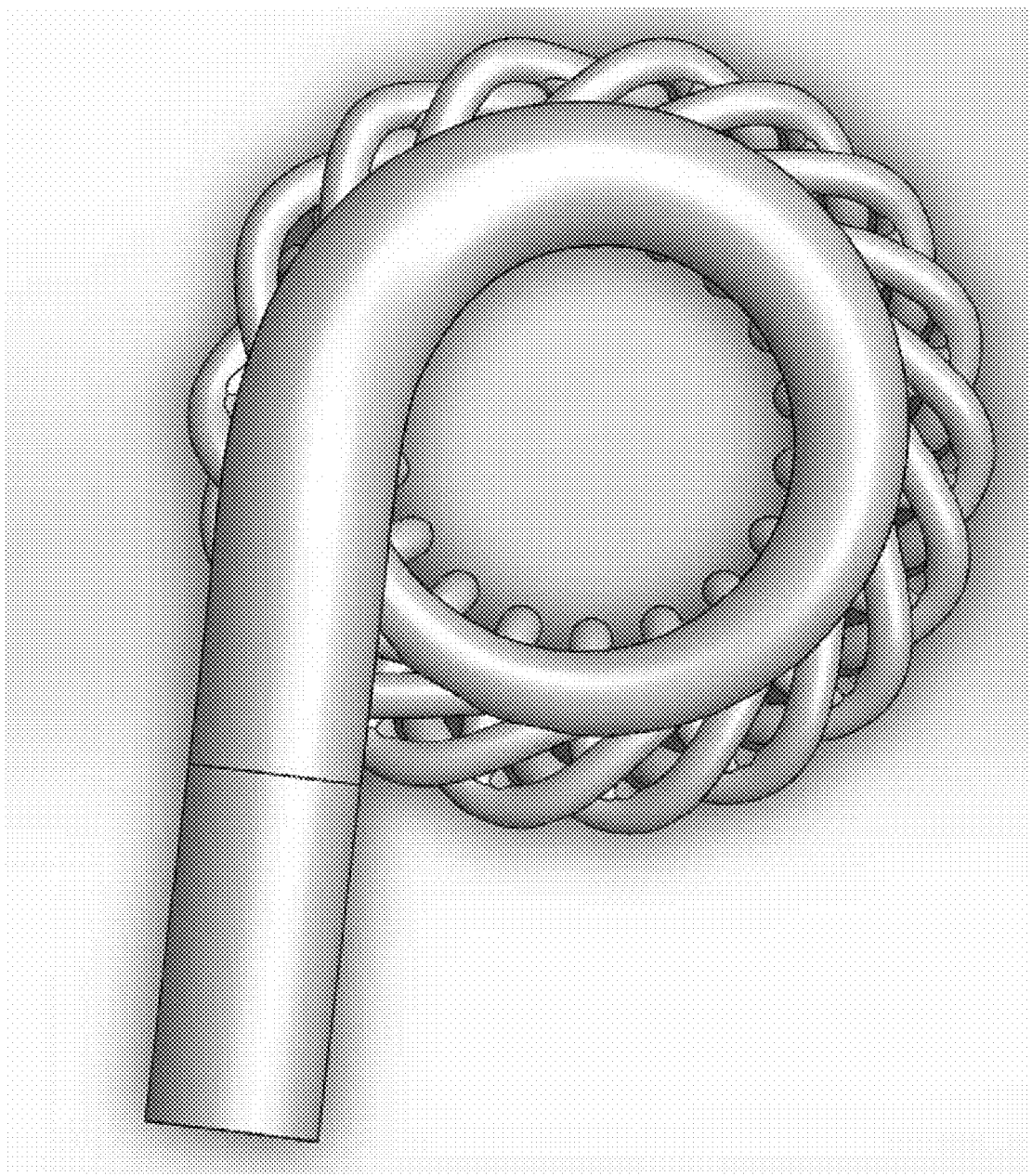
FIGS. 21-26 show various views of another example of a decreasing annulus fluid diverter as part of the design for the fractal fluid passages leading to the injector orifices, according to some embodiments.
Figure 22:
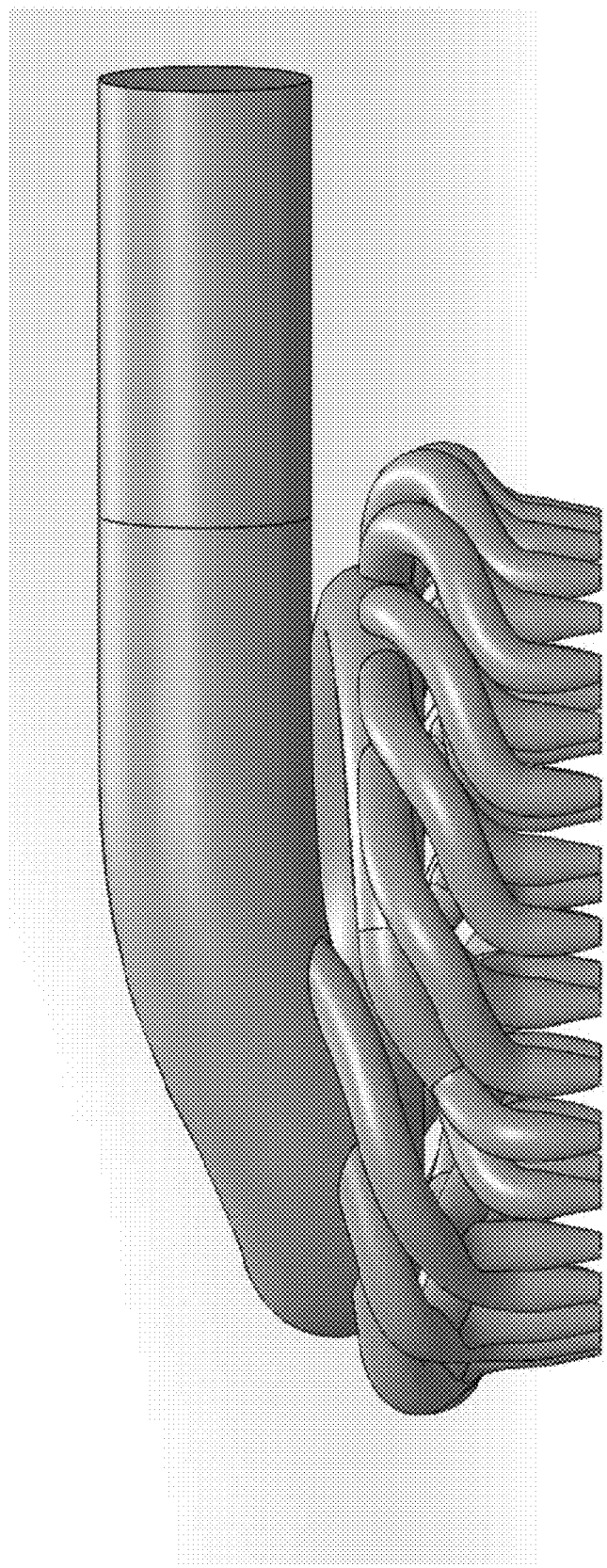
Figure 23:
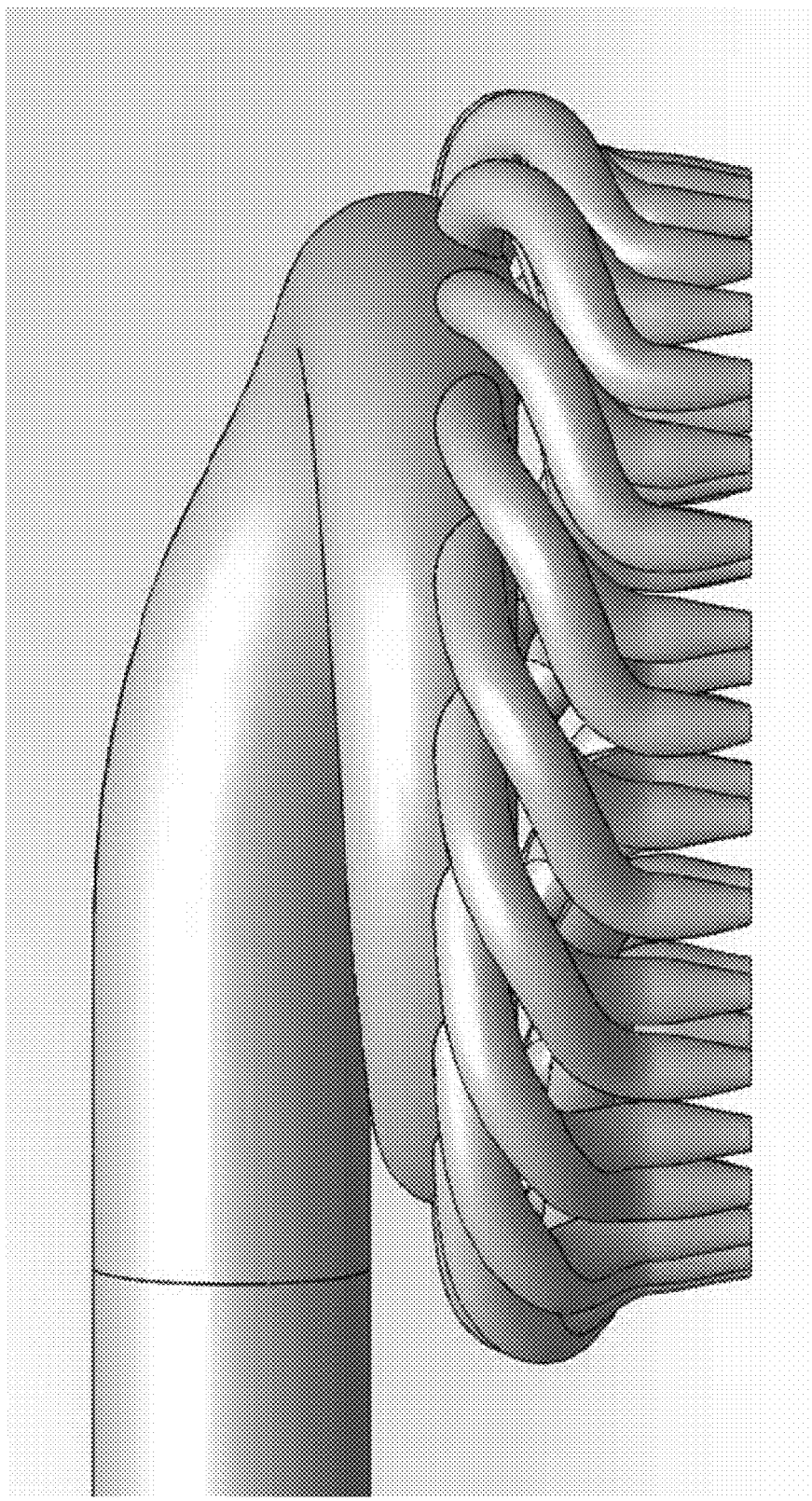
Figure 24:
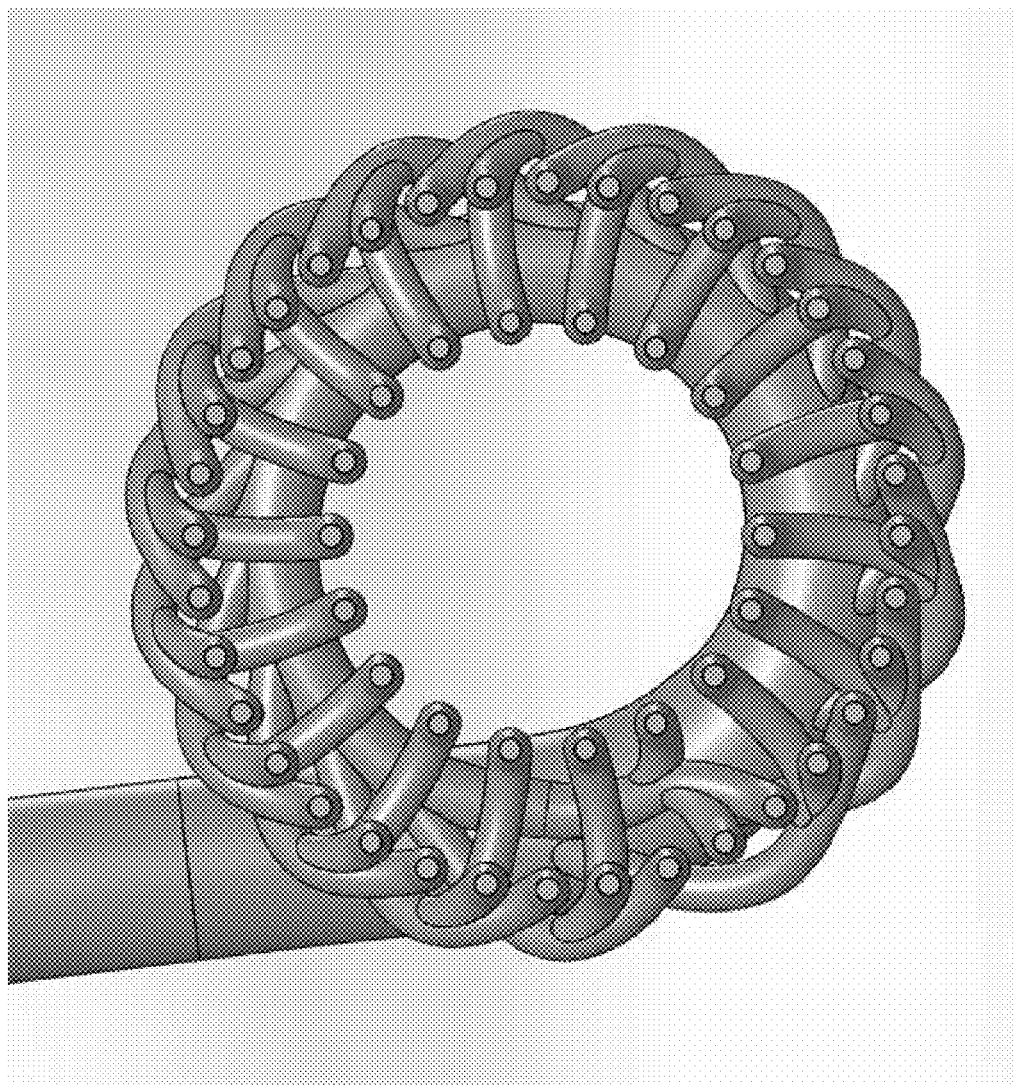
Figure 25:
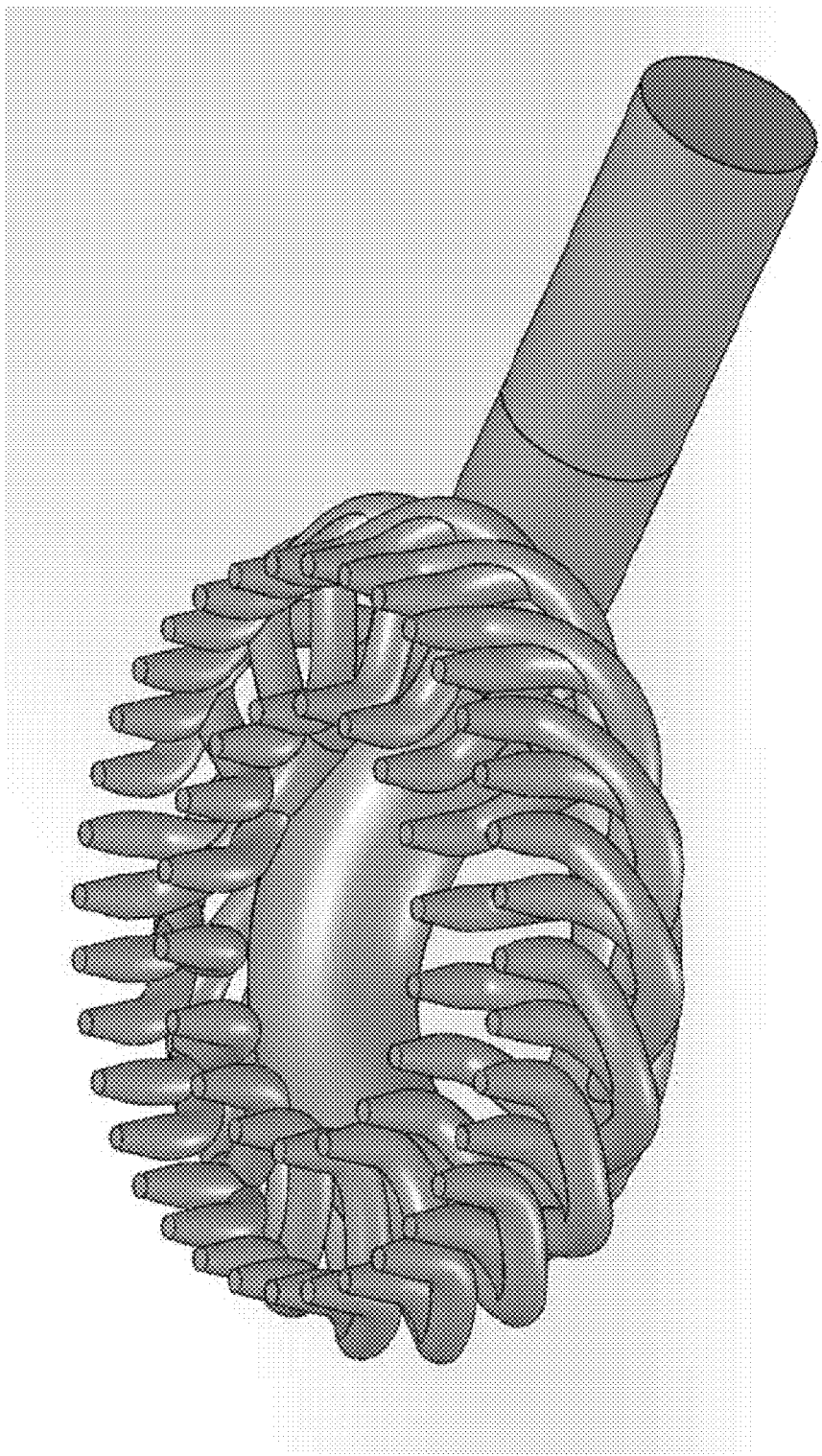
Figure 26:
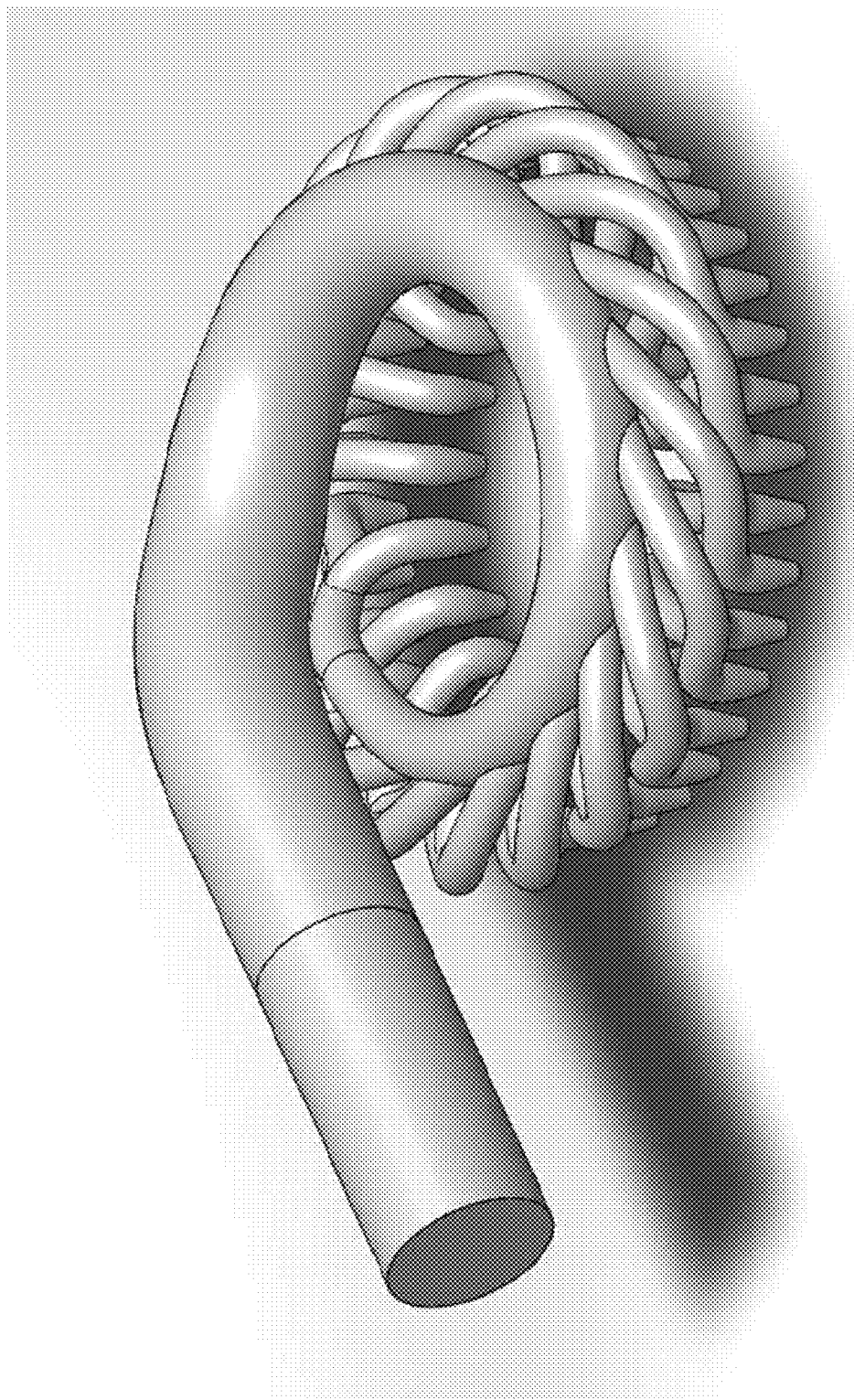

FIG. 21 shows a top-down view of this example fluid diverter. From here, it can be seen how the diverter decreases in radius over its length. FIG. 22 shows one side view of a CAD rendering of this example fluid diverter employed in the liquid oxidizer fluid passages design. As shown, the main fluid passage is largest at the beginning, and becomes decreasingly smaller radially the farther along the fluid travels. FIG. 23 shows an opposite side view of the CAD rendering from FIG. 22. FIG. 24 shows a bottom-up view of this example fluid diverter employed in the liquid oxidizer fluid passages design. From here, it can be seen how each passage from the diverter branches out into three injector orifices. All three of the injector orifices originate from a passage starting at a wider radius from the center. One of the orifices for each branch is positioned to inject fluid more towards the inside of the circular area. Contrast this with the design as shown in FIG. 18, wherein the inner orifice originates from an inner position of the fuel diverter, while the other two outer orifices originate from an outer position of the fuel diverter. Due to the principles of angular momentum, the fluid distributions of these inner orifices of these two designs vary, based on where the fuel originates from in the diverter. FIG. 25 shows a perspective upside-down view of the diverter. FIG. 26 shows a top-down view of this example fluid diverter employed in the liquid oxidizer fluid passages design.

Embodiments of the present disclosure also include example techniques for producing any and all of the various components of the structural heat exchanger embodiments as described herein. In addition, embodiments also include any and all software or other computer-readable media used to program machines for manufacturing said components, and embodiments are not so limited. For example, in some embodiments, a series of boundary conditions are used to guide the shapes and nuances of various fractal designs. An iterative CFD flow simulation may be conducted to measure whether the designed series of passages satisfies the boundary conditions, and may cause gradual changes in the design for adjustments. Smoothing of the channels may be accomplished by gradually modifying successive layers of the apparatus containing the fractal fluid passages.

The following are some examples of boundary conditions that at least some of which may be specified and satisfied during the development of the fractal fluid passages:

Geometric: Inlet flow direction, inlet cross sectional area, outflow element arrangement, outflow direction and target velocities Fluid: Ambient/Initial Temperatures, Mass Flow Rate(s), Surface Roughness, Radiative Heating/Cooling, allowable pressure drop Structural: Internal Pressure, Channel Pressure, External Pressure, Structural Loadings Acoustic: Ambient vibration spectra, frequencies of concern Material Properties of Fluid: Viscosity, Density, Thermal Conductivity, Thermal Diffusivity, Emissivity, Melting/Boiling Point, Heat Capacity and Specific Heat For example, in some embodiments, the fractal fluid passages may be designed to maintain equal cross-sectional area at every layer of the passages, such that the overall cross-sectional area of the initial inlet is equal to the sum of the cross-sectional areas of all of the branching passages at any given cross section.

As another example, in some embodiments, the sizes of the orifices may be varied in order to satisfy predetermined mass flows of the fluid upon exiting the orifices. In other words, when generating a specific structure with fractal fluid passages, boundary conditions may include some orifices requiring mass flows of a certain amount, while other orifices require mass flows of a second amount, and so on for additional sets (or individuals) of orifices. Through the design simulations, a particular design of fractal fluid passages may be generated to meet these predetermined targeted mass flows, using differently sized orifices to achieve that, for example. Even more generally, in some embodiments, the fractal fluid passages may be defined simply by a predetermined inlet mass flow, and predetermined outlet (e.g., orifice) mass flows, where sometimes these outlet mass flows may be defined individually and specifically. The fractal fluid passages having smooth curvature at the branching points may be used to help reliably achieve these specific mass flows, all the while having uniform pressure drop for a given cross-sectional area of the passages. In other words, the exact specific shapes and angles of the passages are not critical and can vary, as long as the fractal fluid passages apparatus satisfies these boundary conditions.

In general, the disclosures herein may also be applied to other applications having various industrial applicability. For example, lossless fractal fluid passages concepts may be applied to HVAC, water pumps, agricultural injectors, and pharmaceutical injectors. As another example, the optimized fluid diverter may similarly be applied to HVAC, water pumps, agricultural injectors, gas turbines, and pharmaceutical injectors. As yet another example, the high stability injector interfaces and designs may be applied to HVAC, water pumps, agricultural injectors, gas turbines, and pharmaceutical injectors. The element pattern of the injector interface may similarly be applied to mixing injector and combustor injector interfaces.

The fractal fluid passages of the present disclosure may allow for moving distributing fluid with little to no pressure drop. This effect may have uses in the following non-exhaustive areas:
  Automotive
    air intake
    exhaust manifold
    fuel injection
  Turbomachinery
    injectors
  Valves
    manifold valves The fractal fluid passages of the present disclosure may allow for efficient spray atomization, mixing and stability. This effect may have uses in the following non-exhaustive areas:
  Internal Combustion Engines/Gas Combustors
    injectors
  Rocket Engines
    injectors The fractal fluid passages of the present disclosure may allow for accurate fluid distribution for mixing and dosing. This effect may have uses in the following non-exhaustive areas:
  Chemical handling, Pharmaceutical and Agricultural
    injectors
    dosing pumps
    fluid dispersion systems
  Aerospace
    Turbine engines
    Turbo pumps
    Rocket engine cooling systems Unless specifically stated otherwise, the terms "a" or "an" are herein used, as is common in patent documents, to include one or more than one instance. Finally, as used herein, the conjunction "or" refers to a non-exclusive "or," unless specifically stated otherwise.

The present disclosure is illustrative and not limiting. Further modifications will be apparent to one skilled in the art in light of this disclosure and are intended to fall within the scope of the appended claims.

What is claimed is:

1. An apparatus comprising:
   a plurality of fractal fluid passages comprising:
     an inlet;
     a first fractal fluid branching passage and a second fractal fluid branching passage, the first and second fractal fluid branching passages coupled to the inlet with continuously smooth curvature to the inlet that minimizes a pressure drop by a fluid flowing from the inlet into both the first and second fractal fluid branching passages;
     a third fractal fluid branching passage and a fourth fractal fluid branching passage, the third and fourth fractal fluid branching passages coupled to the first fractal fluid branching passage with continuously smooth curvature to the first fractal fluid branching passage that minimizes a pressure drop by the fluid flowing from the first fractal fluid branching passage into both the third and fourth fractal fluid branching passages; and
     a fifth fractal fluid branching passage and a sixth fractal fluid branching passage, the fifth and sixth fractal fluid branching passages coupled to the second fractal fluid branching passage with continuously smooth curvature to the second fractal fluid branching passage that minimizes a pressure drop by the fluid flowing from the second fractal fluid branching passage into both the fifth and sixth fractal fluid branching passages;
   wherein the plurality of fractal fluid passages are additively manufactured; and
   wherein at least one of the first, second, third, fourth, fifth, and sixth fractal fluid branching passages comprises an asymmetry in its passage structure configured to reduce an amplitude of a pressure wave propagating through the apparatus.

2. The apparatus of claim 1, further comprising:
   a first orifice leading out an end of the third fractal fluid branching passage;
   a second orifice leading out an end of the fourth fractal fluid branching passage;
   a third orifice leading out an end of the fifth fractal fluid branching passage;
   a fourth orifice leading out an end of the sixth fractal fluid branching passage; and
   wherein each of the first, second, third, and fourth orifices are configured to allow the fluid to exit the plurality of fractal fluid passages at a substantially uniform mass flow.

3. The apparatus of claim 2, wherein the third fractal fluid branching passage is angled differently than the fifth fractal fluid branching passage such that the fluid exiting from the first orifice is ejected at a different angle than the fluid exiting from the third orifice.

4. The apparatus of claim 2, wherein each of the first, second, third, and fourth orifices are configured to allow the fluid to exit the plurality of fractal fluid passages at a uniform velocity.

5. The apparatus of claim 1, wherein:
the inlet comprises an inlet cross-sectional area;
the first fractal fluid branching passage comprises a first cross-sectional area;
the second fractal fluid branching passage comprises a second cross-sectional area;
the third fractal fluid branching passage comprises a third cross-sectional area;
the fourth fractal fluid branching passage comprises a fourth cross-sectional area;
the fifth fractal fluid branching passage comprises a fifth cross-sectional area;
the sixth fractal fluid branching passage comprises a sixth cross-sectional area;
the sum of the first cross-sectional area and the second cross-sectional area equals the inlet cross-sectional area; and
the sum of the third cross-sectional area, the fourth cross-sectional area, the fifth cross-sectional area and the sixth cross-sectional area equals the inlet cross-sectional area.

6. The apparatus of claim 1, wherein the fluid flows through each of the inlet, the first fractal fluid branching passage, the second fractal fluid branching passage, the third fractal fluid branching passage, the fourth fractal fluid branching passage, the fifth fractal fluid branching passage, and the sixth fractal fluid branching passage at a uniform velocity.

7. The apparatus of claim 1, wherein the fluid flows through each of the inlet, the first fractal fluid branching passage, the second fractal fluid branching passage, the third fractal fluid branching passage, the fourth fractal fluid branching passage, the fifth fractal fluid branching passage, and the sixth fractal fluid branching passage at a uniform pressure.

8. The apparatus of claim 1, further comprising:
a first orifice leading out an end of the third fractal fluid branching passage;
a second orifice leading out an end of the fourth fractal fluid branching passage;
a third orifice leading out an end of the fifth fractal fluid branching passage;
a fourth orifice leading out an end of the sixth fractal fluid branching passage;
wherein:
the first orifice is configured to allow the fluid to exit the plurality of fractal fluid passages at a first predetermined mass flow;
the second orifice is configured to allow the fluid to exit the plurality of fractal fluid passages at a second predetermined mass flow;
the third orifice is configured to allow the fluid to exit the plurality of fractal fluid passages at a third predetermined mass flow; and
the fourth orifice is configured to allow the fluid to exit the plurality of fractal fluid passages at a fourth predetermined mass flow.

9. The apparatus of claim 1, wherein the first fractal fluid branching passage, the second fractal fluid branching passage, the third fractal fluid branching passage, the fourth fractal fluid branching passage, the fifth fractal fluid branching passage, and the sixth fractal fluid branching passage are asymmetrically shaped from one another.

10. The apparatus of claim 1, wherein the plurality of fractal fluid passages is a first plurality of fractal fluid passages, and the fluid is a first fluid,
wherein the apparatus further comprises a second plurality of fractal fluid passages configured to allow a second fluid different from the first fluid to flow through the second plurality of fractal fluid passages simultaneously with the flow of the first fluid through the first plurality of fractal fluid passages.

11. The apparatus of claim 10, further comprising an injector interface partially enclosing a chamber and comprising a first plurality of orifices such that the first fluid exits the first plurality of fractal fluid passages through the injector interface and into the chamber via the first plurality of orifices.

12. The apparatus of claim 11, wherein the second plurality of fractal fluid passages comprises a second plurality of orifices, and the injector interface further comprises the second plurality of orifices such that the second fluid exits the second plurality of fractal fluid passages through the injector interface and into the chamber via the second plurality of orifices.

13. The apparatus of claim 12, wherein the second fluid exits the injector interface via at least a portion of the second plurality of orifices at a different angle than the first fluid exiting the injector interface.

14. The apparatus of claim 13, wherein at least a portion of the second fluid exits the injector interface at an angle toward the first orifice of the first plurality of fractal fluid passages such that at least said portion of the second fluid collides with the first fluid exiting the first orifice through the injector interface.

15. The apparatus of claim 1, wherein the plurality of fractal fluid passages further comprises a seventh fractal fluid branching passage and an eighth fractal fluid branching passage, wherein:
the seventh fractal fluid branching passage is coupled to the first fractal fluid branching passage with continuously smooth curvature to the first fractal fluid branching passage that minimizes a pressure drop by the fluid flowing from the first fractal fluid branching passage into the seventh fractal fluid branching passage; and
the eighth fractal fluid branching passage is coupled to the second fractal fluid branching passage with continuously smooth curvature to the second fractal fluid branching passage that minimizes a pressure drop by the fluid flowing from the second fractal fluid branching passage into the eighth fractal fluid branching passage.

16. An apparatus comprising:
a first plurality of fractal fluid passages comprising:
an inlet;
a first fractal fluid branching passage and a second fractal fluid branching passage, the first and second fractal fluid branching passages coupled to the inlet with continuously smooth curvature to the inlet that minimizes a pressure drop by a first fluid flowing from the inlet into both the first and second fractal fluid branching passages;
a third fractal fluid branching passage and a fourth fractal fluid branching passage, the third and fourth fractal fluid branching passages coupled to the first fractal fluid branching passage with continuously smooth curvature to the first fractal fluid branching passage that minimizes a pressure drop by the first fluid flowing from the first fractal fluid branching passage into both the third and fourth fractal fluid branching passages; and
a fifth fractal fluid branching passage and a sixth fractal fluid branching passage, the fifth and sixth fractal fluid branching passages coupled to the second fractal fluid branching passage with continuously smooth curvature to the second fractal fluid branching passage that minimizes a pressure drop by the first fluid flowing from the second fractal fluid branching passage into both the fifth and sixth fractal fluid branching passages;
a second plurality of fractal fluid passages configured to allow a second fluid different from the first fluid to flow through the second plurality of fractal fluid passages simultaneously with the flow of the first fluid through the first plurality of fractal fluid passages; and
a plurality of regenerative cooling channels;
wherein the second plurality of fractal fluid passages is coupled to the plurality of regenerative cooling channels such that the second fluid is configured to flow through the plurality of regenerative cooling channels and into the second plurality of fractal fluid passages.

17. An apparatus comprising:
a first plurality of fractal fluid passages comprising:
  an inlet;
  a first fractal fluid branching passage and a second fractal fluid branching passage, the first and second fractal fluid branching passages coupled to the inlet with continuously smooth curvature to the inlet that minimizes a pressure drop by a first fluid flowing from the inlet into both the first and second fractal fluid branching passages;
  a third fractal fluid branching passage and a fourth fractal fluid branching passage, the third and fourth fractal fluid branching passages coupled to the first fractal fluid branching passage with continuously smooth curvature to the first fractal fluid branching passage that minimizes a pressure drop by the first fluid flowing from the first fractal fluid branching passage into both the third and fourth fractal fluid branching passages; and
  a fifth fractal fluid branching passage and a sixth fractal fluid branching passage, the fifth and sixth fractal fluid branching passages coupled to the second fractal fluid branching passage with continuously smooth curvature to the second fractal fluid branching passage that minimizes a pressure drop by the first fluid flowing from the second fractal fluid branching passage into both the fifth and sixth fractal fluid branching passages;
a second plurality of fractal fluid passages configured to allow a second fluid different from the first fluid to flow through the second plurality of fractal fluid passages simultaneously with the flow of the first fluid through the first plurality of fractal fluid passages;
wherein:
  a first fractal fluid passage of the second plurality of fractal fluid passages comprises a first portion of the passage configured to cause the second fluid to flow in a direction the same as a first direction of the first plurality of fractal fluid passages; and
  said first fractal fluid passage of the second plurality of fractal fluid passages further comprises a second portion of the passage configured to cause the second fluid to flow in a direction opposite as the first direction of the first plurality of fractal fluid passages.

18. An apparatus comprising:
a first plurality of fractal fluid passages comprising:
  an inlet;
  a first fractal fluid branching passage and a second fractal fluid branching passage, the first and second fractal fluid branching passages coupled to the inlet with continuously smooth curvature to the inlet that minimizes a pressure drop by a first fluid flowing from the inlet into both the first and second fractal fluid branching passages;
  a third fractal fluid branching passage and a fourth fractal fluid branching passage, the third and fourth fractal fluid branching passages coupled to the first fractal fluid branching passage with continuously smooth curvature to the first fractal fluid branching passage that minimizes a pressure drop by the first fluid flowing from the first fractal fluid branching passage into both the third and fourth fractal fluid branching passages; and
  a fifth fractal fluid branching passage and a sixth fractal fluid branching passage, the fifth and sixth fractal fluid branching passages coupled to the second fractal fluid branching passage with continuously smooth curvature to the second fractal fluid branching passage that minimizes a pressure drop by the first fluid flowing from the second fractal fluid branching passage into both the fifth and sixth fractal fluid branching passages;
a second plurality of fractal fluid passages configured to allow a second fluid different from the first fluid to flow through the second plurality of fractal fluid passages simultaneously with the flow of the first fluid through the first plurality of fractal fluid passages; and
a fluid diverter comprising an annulus with progressively decreasing cross-sectional area;
wherein the first plurality of fractal fluid passages are additively manufactured.

19. An apparatus comprising:
a plurality of fractal fluid passages comprising:
  an inlet;
  a fluid diverter coupled to the inlet and comprising an annulus with progressively decreasing cross-sectional area;
  a first fractal fluid branching passage coupled to the fluid diverter;
  a second fractal fluid branching passage coupled to the fluid diverter and having an equal cross-sectional area to the first fractal fluid branching passage;
  a third fractal fluid branching passage and a fourth fractal fluid branching passage, the third and fourth fractal fluid branching passages coupled to the first fractal fluid branching passage with continuously smooth curvature to the first fractal fluid branching passage that minimizes a pressure drop by the fluid flowing from the first fractal fluid branching passage into both the third and fourth fractal fluid branching passages; and
  a fifth fractal fluid branching passage and a sixth fractal fluid branching passage, the fifth and sixth fractal fluid branching passages coupled to the second fractal fluid branching passage with continuously smooth curvature to the second fractal fluid branching passage that minimizes a pressure drop by the fluid flowing from the second fractal fluid branching passage into both the fifth and sixth fractal fluid branching passages.

20. The apparatus of claim 19, wherein fluid is configured to flow from the inlet and into the fluid diverter, then into the first fractal fluid branching passage, and then into the second fractal fluid branching passage; and wherein the fluid flows into the first and second fractal fluid branching passages with uniform pressure simultaneously.

* * * * *